(12) United States Patent
Nikolov et al.

(10) Patent No.: US 10,501,553 B2
(45) Date of Patent: Dec. 10, 2019

(54) METHODS AND COMPOSITIONS FOR CANCER TREATING CONDITIONS RELATING TO OVER EXPRESSIONS OF EPHA2

(71) Applicants: MEMORIAL SLOAN-KETTERING CANCER CENTER, New York, NY (US); University of Turku, Turku (FI)

(72) Inventors: Dimitar B Nikolov, New York, NY (US); Juha Himanen, New York, NY (US); Urpo Lamminmaki, Lieto (FI); Hanna Sanmark, Turku (FI)

( * ) Notice: Subject to any disclaimer, the term of this patent is extended or adjusted under 35 U.S.C. 154(b) by 61 days.

(21) Appl. No.: 15/528,073

(22) PCT Filed: Nov. 18, 2015

(86) PCT No.: PCT/US2015/061345
§ 371 (c)(1),
(2) Date: May 18, 2017

(87) PCT Pub. No.: WO2016/081601
PCT Pub. Date: May 26, 2016

(65) Prior Publication Data
US 2017/0349663 A1 Dec. 7, 2017

Related U.S. Application Data

(60) Provisional application No. 62/082,020, filed on Nov. 19, 2014.

(51) Int. Cl.
| | |
|---|---|
| C07K 16/28 | (2006.01) |
| C07K 16/46 | (2006.01) |
| A61K 39/395 | (2006.01) |
| C07K 16/30 | (2006.01) |
| C07K 14/705 | (2006.01) |
| A61K 39/00 | (2006.01) |

(52) U.S. Cl.
CPC ........ *C07K 16/2887* (2013.01); *A61K 39/395* (2013.01); *A61K 39/3955* (2013.01); *C07K 16/2866* (2013.01); *C07K 16/2896* (2013.01); *C07K 16/30* (2013.01); *C07K 16/468* (2013.01); *A61K 2039/505* (2013.01); *A61K 2039/545* (2013.01); *C07K 2317/31* (2013.01); *C07K 2317/622* (2013.01); *C07K 2317/73* (2013.01); *C07K 2317/76* (2013.01); *C07K 2319/00* (2013.01)

(58) Field of Classification Search
CPC .......... A61K 2039/505; A61K 39/3955; A61K 39/39558; C07K 2317/622; C07K 2317/565; C07K 2317/76; C07K 2317/56; C07K 2317/73; C07K 16/30; C07K 16/2896; C07K 16/18; C07K 2319/00; C07K 2317/569
See application file for complete search history.

(56) References Cited

U.S. PATENT DOCUMENTS

| | | | |
|---|---|---|---|
| 2007/0086943 A1 | 4/2007 | Kinch et al. | |
| 2008/0044413 A1* | 2/2008 | Hammond | C07K 16/2809 424/135.1 |
| 2009/0304721 A1* | 12/2009 | Kinch | C07K 16/2866 424/183.1 |
| 2010/0034820 A1 | 2/2010 | Ledbetter et al. | |
| 2010/0172868 A1* | 7/2010 | Morrison | A61K 38/212 424/85.4 |
| 2010/0279932 A1* | 11/2010 | Ledbetter | C07K 16/2818 514/7.3 |
| 2010/0330089 A1 | 12/2010 | Damle et al. | |
| 2013/0165629 A1* | 6/2013 | Hsu | C07K 7/06 530/326 |

FOREIGN PATENT DOCUMENTS

| | | |
|---|---|---|
| WO | 2006047638 A2 | 5/2006 |
| WO | 2012012759 A2 | 1/2012 |
| WO | 2012040323 A2 | 3/2012 |

OTHER PUBLICATIONS

Ahmadzadeh et al. Design, expression and characterization of a single chain anti-CD20 antibody; a germline humanized antibody derived from Rituximab. Protein Exp Purification 102: 45-51, 2014.*
Fang et al. Antitumor effects of an engineered and energized fusion protein consisting of an anti-CD20 scFv fragment and lidamycin . Sci China Life Sci 54: 255-262, 2011.*
Hammond et al. Selective targeting and potent control of tumor growth using an EphA2/CD3-bispecific single-chain antibody construct. Cancer Res 67(8): 3927-3935, 2007.*
Jachimowicz et al. Multi-specific antibodies for cancer therapy. BioDrugs 28: 331-343, 2014.*
Kellner et al. Fusion proteins between ligands for NKG2 and CD20-directed single-chain variable fragments sensitize lymphoma cells for natural killer cell-mediated lysis and enhance antibody-dependent cellular cytotoxicity. Leukemia 26: 830-834, 2012.*
Lamminmaki et al. Eph receptors as drug targets: single-chain antibodies and beyond. Curr Drug Targets 16: 1021-1030, 2015.*
PosthumaDeBoer et al. Surface proteomic analysis of osteosarcoma identifies EPHA2 as receptor for targeted drug delivery. Brit J Cancer 109: 2142-2154, 2013.*
Saha et al. Therapeutic potential of targeting the Eph/ephrin signaling complex. Int J Biochem Cell Biol 105: 123-133, 2018.*

(Continued)

*Primary Examiner* — Bridget E Bunner
(74) *Attorney, Agent, or Firm* — Grimes & Yvon LLP

(57) ABSTRACT

An anti-EphA2 scFv single-chain antibody binds with high specificity for EphA2 and blocks ephrin binding to Eph-A2. The antibody may be linked with other antigen-targeting domains, such as an anti-CD20 domain, or conjugated with toxins, or used in combination therapy to for treatment of conditions related to overexpression of EphA2. The antibody may also be expressed in vivo by an expression vector that is designed to facilitate such treatment.

27 Claims, 9 Drawing Sheets
Specification includes a Sequence Listing.

(56) References Cited

OTHER PUBLICATIONS

Shan et al. Characterization of scFv-Ig constructs generated from the anti-CD20 mAb 1F5 using linker peptides of varying lengths. J Immunol 162: 6589-6595, 1999.*

Wang et al. Delivery of an miR155 inhibitor by anti-CD20 single-chain antibody into B cells reduces the acetylcholine receptor-specific autoantibodies and ameliorates experimental autoimmune myasthenia gravis. Clin Exp Immunol 176: 207-221, 2014.*

Yan et al. Human umbilical cord mesenchymal stem cells as vehicles of CD20-specific TRAIL fusion protein delivery: a double-target therapy against non-Hodgkin's Lymphoma. Mol Pharmaceutics 10: 142-151, 2013.*

Yu et al. Immunotherapy of lymphomas with T cells modified by anti-CD20 scFv/CD28/CD3zeta recombinant gene. Leukemia Lymphoma 49(7): 1368-1373, 2008.*

International Search Report and Written Opinion dated Apr. 7, 2016 for PCT application PCT/US2015/061345.

Oricchio et al., "The Eph-Receptor is a Soluble Tumor Suppressor for Follicular Lymphoma" Cell, Cell Press, Amsterdam, NL, vol. 147, No. 3, Sep. 21, 2011 (Sep. 21, 2011), pp. 554-564.

Goldgur et al., "Generation and characterization of a single-chain anti-EphA2 antibody," GRowth Factors. vol. 32, No. 6, Nov. 19, 2014 (Nov. 19, 2014), pp. 214-222.

Fang et al., "Antitumor effects of an engineered and energized fusion protein consisting of an anti-CD20 scFv fragment and lidamycin," Science China Life Sciences, Science China Press, Heidelberg, vol. 54, No. 3, Mar. 16, 2011 (Mar. 16, 2011), pp. 255-262.

* cited by examiner

A

B

METHODS AND COMPOSITIONS FOR CANCER TREATING CONDITIONS RELATING TO OVER EXPRESSIONS OF EPHA2

This application claims priority to U.S. Provisional Patent Application Ser. No. 62/082,020, filed Nov. 19, 2014. The entirety of the aforementioned application is incorporated herein by reference.

This invention was made with government support under grant number RO1NS038486 awarded by the National Institute of Health. The government has certain rights in the invention.

FIELD

The present invention relates to compositions and methods for isolating specific antibodies and methods of treating disorders with antibodies.

BACKGROUND

Monoclonal antibodies (mAb's) are important tools in research, diagnostics, and therapy. MAb's with suitable specificities can be highly valuable tools for the modulation of cell signaling and have great potential as cancer therapeutics. Typically, mAb's are prepared using hydridoma cell lines. Generation of such mAbs with desired specificity, however, is difficult when the target antigen or epitope is conserved between human and mouse. Another issue complicating the development of therapeutic mAbs is the fact that the successful outcome of the humanization process, generally implemented to reduce the immunogenicity of the rodent protein, cannot be guaranteed. In addition, commercially available mAbs for research are well known to often have serious quality issues, where one batch of the antibody functions quite differently from another batch from the same manufacturer. There is a constant need of good-quality antibodies for biochemical, structural and functional studies.

The ephrin (Eph) receptors have been sought as therapeutic targets in liquid and solid tumors. Eph receptors are a subcategory of receptor tyrosine kinases, and they therefore play vital parts in cell survival and function. Notably, the receptors within the Eph family are also extremely highly conserved between species, generally having only two-three amino acids differences between the human and mouse proteins. In such instances it is virtually impossible to create antibodies using the classical murine technology.

EphA2 is a sensory receptor protein on the surface of both normal and cancerous lymphocytes and is a potential therapeutic target for lymphoma. Inappropriate activation of EphA2 is known to be the cause of follicular and other lymphomas. Follicular lymphoma is a common and incurable form of B-cell lymphoma. Current lymphoma therapeutics show only modest effect against follicular lymphoma and new therapeutics are needed. EphA2 has also been described to be important for the survival in EphA2-positive mouse leukemia models and not essential for normal hematopoiesis. Acute myelogenous leukemia (AML) is another disease with dismal outcomes and thus identification on new therapeutic targets is needed.

SUMMARY

One aspect of the present application relates to a fusion protein, comprising: an anti-EphA2 scFv domain; an anti-CD20 scFV domain; and a peptide linker connecting the anti-EphA2 scFv domain to the anti-CD20 scFV domain. In some embodiments, the anti-EphA2 scFv domain comprises an amino acid sequence of SEQ ID NO:1, 5, 6 or 7, or an amino acid sequence of a functional variant of SEQ ID NO:1, 5, 6 or 7. In some embodiments, the anti-CD20 scFV domain comprises an amino acid sequence of SEQ ID NO:3, or an amino acid sequence of a functional variant of SEQ ID NO:3. In some embodiments, the fusion protein comprises the amino acid sequence of SEQ ID NO:9. In some embodiments, the fusion protein further comprises an N-terminal signal peptide sequence suitable for secretion of the fusion protein Another aspect of the present application relates to a polynucleotide encoding the fusion protein of the present application.

Another aspect of the present application relates to an expression vector comprising the polynucleotide of the present application, wherein the polynucleotide is operably linked to one or more regulatory sequences sufficient for expressing the fusion protein of the present application in a cell. In some embodiments, the expression vector is a virus vector. In other embodiments, the expression vector is a plasmid vector.

Another aspect of the present application relates to a method for treating a proliferative disorder, comprising administering to a subject in need thereof an effective amount of an antibody comprising an anti-EphA2 scFv domain. In some embodiments, the antibody comprises an amino acid sequence of SEQ ID NO:1, 5, 6 or 7. In some embodiments, the antibody is a bispecific fusion antibody comprising an anti-EphA2 scFv domain, an anti-CD20 scFV domain, and a peptide linker connecting the anti-EphA2 scFv domain to the anti-CD20 scFV domain. In some embodiments, the antibody comprises an amino acid sequence of SEQ ID NO:1 or SEQ ID NO:9, and the proliferative disorder is acute myelogenous leukemia (AML).

Another aspect of the present application relates to a method for treating an autoimmune disease or an alloimmune response, comprising administering to a subject in need thereof an effective amount of an antibody comprising an anti-EphA2 scFv domain.

BRIEF DESCRIPTION OF THE DRAWINGS

FIG. 5A, Apoptosis analysis in Raji, Ly19 and Toledo lymphoma cell lines treated for 24 h with 1 ug/ml or 5 ug/ml of D2 scFv. FIG. 5B, Cell proliferation analysis were performed every 24 h in Raji lymphoma cell line treated with vehicle as control or 1 ug/ml, 5 ug/ml, or 10 ug/ml of D2scFv.

DETAILED DESCRIPTION

Figure 1A:
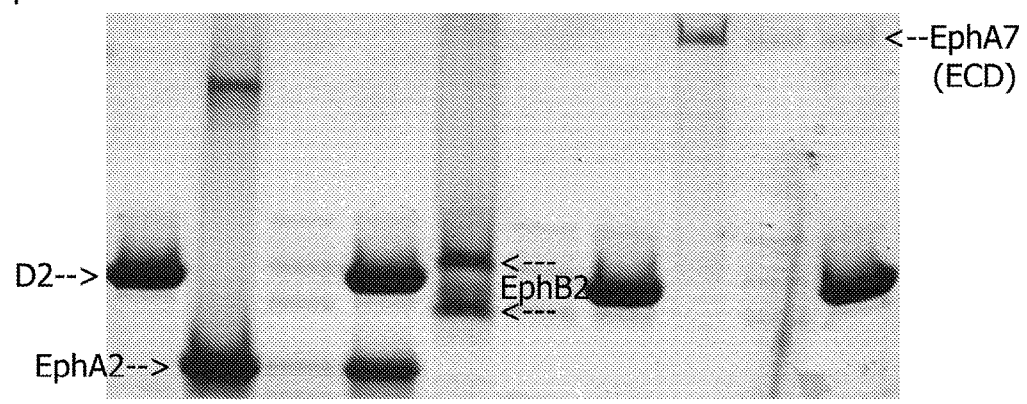
FIG. 1A is a picture showing a pull-down assay to evaluate the binding of EphA2 to the D2-scFv. D2-scFv is able to pull down untagged EphA2 but not EphB2 or EphA7. The result confirms the binding specificity of the D2 for EphA2.

Some modes for carrying out the present invention are presented in terms of its exemplary embodiments, herein discussed below. However, the present invention is not limited to the described embodiment and a person skilled in the art will appreciate that many other embodiments of the present invention are possible without deviating from the basic concept of the present invention, and that any such work around will also fall under scope of this application. It is envisioned that other styles and configurations of the present invention can be easily incorporated into the teachings of the present invention, and only one particular configuration shall be shown and described for purposes of clarity and disclosure and not by way of limitation of scope.

Headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). The terms "a" and "an" herein do not denote a limitation of quantity, but rather denote the presence of at least one of the referenced items.

Definitions

The term "proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is a neoplasm or tumor, which is an abnormal growth of tissue. As used herein, the term "cancer" or "tumor" refers to any of the various or pre-malignant (e.g., benign tumor and atypical hyperplasia) or malignant (e.g., cancer) neoplasms characterized by the proliferation of cells that have the capability to invade surrounding tissue and/or metastasize to new colonization sites, including but not limited to leukemias, lymphomas, carcinomas, melanomas, sarcomas, germ cell tumors and blastomas. Exemplary cancers include cancers of the brain, bladder, breast, cervix, colon, head and neck, kidney, lung, non-small cell lung, mesothelioma, ovary, prostate, stomach and uterus, leukemia and medulloblastoma. Cancer can originate from any cell type or tissue found in a mammal, including, but not limited to hepatic, skin, breast, prostate, neural, optic, intestinal, cardiac, vasculature, lymph, spleen, renal, bladder, lung, muscle, connective, tissue, pancreatic, pituitary, endocrine, reproductive organs, bone, and blood.

The term "leukemia" refers to broadly progressive, malignant diseases of the blood-forming organs and is generally characterized by a distorted proliferation and development of leukocytes and their precursors in the blood and bone marrow. Leukemia diseases include, for example, acute myelogenous leukemia (AML), acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "lymphoma" is taken to mean cancers of lymphoid tissue, such as lymph nodes, spleen, and other organs of the immune system. Non-Hodgkin's lymphoma includes, slow-growing lymphomas and lymphoid leukemias of B-cell or T-cell subtypes, such as the B-cell lymophomas, such as B-cell chronic lymphocytic leukemia (B-CLL)/small lymphocytic lymphoma (SLL), lymphoplasmacytoid lymphoma, follicle center lymphoma, follicular small cleaved cell (FSC), follicular mixed cell (FM), marginal zone B-cell lymphoma, hairy cell leukemia, plasmacytoma/myeloma and T-cell lymphomas, including, large granular lymphocyte leukemia, adult T-Cell leukemia/lymphoma (ATL/L), mycosis fungoides/sezary syndrome. Also included are moderately aggressive lymphomas and lymphoid leukemias of B-cell original, e.g., B-cell prolymphocytic leukemia (B-PLL), mantle cell lymphoma, follicle center lymphoma, follicular small cleaved cell (FSC), follicle center lymphoma (follicular large cell) or T-cell origin, T-cell chronic lymphocytic leukemia/prolymphocytic leukemia (T-CLL/PLL), adult T-Cell leukemia/lymphoma (ATL/L) [chronic], angiocentric lymphoma, angioimmunoblastic lymphoma, aggressive lymphomas including, B-cell large B-cell lymphoma, peripheral T-cell lymphomas, intestinal T-cell lymphoma, anaplastic large cell lymphoma, highly aggressive lymphomas and lymphoid leukemias, including precursor B-lymphoblastic leukemia/lymphoma (PB-LBL/L), Burkitt's lymphoma, high-grade B-Cell lymphoma, Burkitt's-like, and precursor T-lymphoblastic leukemia/lymphoma (T-LBL/L), adult T-cell leukemia/lymphoma (ATLL) [acute and lymphomatous], slow-growing (Low Grade) Lymphomas of the B-cell types, e.g., small lymphocytic/pro-lymphocytic lymphoma (SLL), follicular lymphoma (few large cells), lymphoplasmacytoid lymphoma, marginal zone lymphoma, and slow-growing lymphomas of the T-cell subtypes, for example, large granular lymphocyte leukemia, adult T-cell leukemia/lymphoma (ATL/L), and mycosis fungoides/Sezary syndrome.

The term "carcinoma" refers to the malignant growth of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" refers to a tumor made up of a substance like the embryonic connective tissue and is generally composed of closely packed cells embedded in a fibrillar or homogeneous substance. Exemplary sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" refers to a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, thyroid cancer, neuroblastoma, esophageal cancer, genitourinary tract cancer, malignant hypercalcemia, cervical cancer, endometrial cancer, and adrenal cortical cancer.

As used herein, the terms "subject," "individual," and "animal" are used interchangeably herein to refer to a vertebrate, preferably a mammal. The term "mammal" or "mammalian" includes, but is not limited to, murines, simians, humans, farm animals, sport animals, and pets. Tissues, cells and their progeny of a biological entity obtained in vivo or cultured in vitro are also encompassed.

As used herein, the term "linker" is a cross-link between separately originated amino acid sequences or between an amino acid sequence and a small molecule. The linker may be a peptide linker. In some embodiments, the linker is a peptide link between a VH region and a VL region. In some embodiments, a peptide linker consisting of glycine-serine is used. In some embodiments, the linker is a cross-link between two separate scFv domains, for which purpose a peptide linker comprising several amino acids may be used. The peptide linker may be rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. The linker may variable in length, preferably about five to about twenty-five amino acids long. A linker may also be a cleavable or non-cleavable chemical linker for use, for example, in an antibody-drug conjugate.

As used herein, the term "antibody" is meant to include intact antibodies, antibody fragments, e.g., Fab and F(ab')2, and genetically modified antibodies, e.g., scFv antibodies, bispecific fusion antibodies having two scFv domains linked by a peptide linker, diabodies, and dual variable domain (DVD) Igs. An antibody can refer to monoclonal antibodies, polyclonal antibodies, multivalent antibodies, multispecific antibodies, single chain antibodies, human or humanized antibodies, and antibody fragments or other variants that retain the ability to specifically bind a target antigen. Antibodies used in the present application can be purchased commercially or, if necessary or desired, can be generated using techniques well known in the art. The same is true for any antibody useful in the context of the present methods (See, e.g., Antibodies: A Laboratory Manual (Second Edition), Edited by Edward A. Greenfield. 2014, Cold Spring Harbor Laboratory Press). As used herein, the term "bispecific antibody" refers to a single amino acid construct which brings two separate antigen-binding domains together to form a single fusion protein. As used herein, the term "single chain anti-EphA2 antibody" may apply interchangeably to monospecific and bispecific scFv antibodies. As used herein, the term "fusion antibody" broadly refers to any fusion protein described herein, which minimally includes an anti-EphA2 scFv domain and an scFv anti-CD20 scFv domain. In some embodiments, the fusion antibody comprises an anti-EphA2 peptide of SEQ ID NO: 1, 5, 6 or 7, or a functional variant thereof.

As used herein, the term "scFv antibody" or "scFv" or "scFv domain" is an antibody which contains an Fv region, that is, a heavy chain variable region (VH region) and a light chain variable region (VL region), and which is constructed by a cross-linkage of these two regions using a linker, or which regions may be directly connected as fragments without a linker. In specific embodiments, scFvs may include bi-specific scFvs and humanized scFvs.

As used herein, the term "anti-EphA2 scFv domain" refers to a scFv peptide that specifically binds to human EphA2 protein. In some embodiments, the anti-EphA2 scFv domain comprises the amino acid sequence of SEQ ID NO:1, 5, 6 or 7. In some embodiments, the anti-EphA2 scFv domain consists of the amino acid sequence of SEQ ID NO:1, 5, 6 or 7.

As used herein, the term "anti-CD20 scFv domain" refers to a scFv peptide that specifically binds to human CD20 protein. In some embodiments, the anti-CD20 scFv domain comprises the amino acid sequence of SEQ ID NO:9. In some embodiments, the anti-CD20 scFv domain consists of the amino acid sequence of SEQ ID NO:9.

As used herein, the term "function variant" of a peptide refers to a peptide that differs in amino acid sequence from the original peptide but maintains the biological function of the original peptide, e.g., antigen-binding function. In some embodiments, the functional variant maintains at least 70%, 75%, 80%, 85%, 90% or 95% of a biological activity or structure function of the original peptide.

As used herein, the term "anti-EphA2" or "anti-CD20" or "antigen-binding" refers to proteins that are biologically active in that they specifically bind to the target antigen and can compete with other antigen binding proteins, including intact antibodies, for specific binding to a given epitope. The term "compete" when used in the context of antigen binding proteins (e.g., neutralizing antigen binding proteins or neutralizing antibodies) means competition between antigen binding proteins as determined by an assay in which the antigen binding protein (e.g., antibody or immunologically functional fragment thereof) under test prevents or inhibits specific binding of a reference antigen binding protein (e.g., a ligand, or a reference antibody) to a common antigen (e.g., an EphA2 protein or a fragment thereof). The binding of an antigen binding protein may also be described by the region or regions of the antigen that the antigen binding protein interacts with. Such region(s) of interaction may be determined by various methods known in the art. Certain of the antigen binding proteins as provided herein specifically bind to human EphA2 or CD20.

As used herein, the term "specifically bind to" or "bind specifically to" means binding to a target molecule (e.g., an antibody binds to an antigen) with an equilibrium dissociation constant ($K_d$) of less than $10^{-6}$ M, $10^{-7}$ M, $10^{-8}$ M, $10^{-9}$ M or $10^{-10}$ M. Similarly, an antigen-specific antibody, such as EphA2-specific antibody or CD20-specific antibody, refers to an antibody that binds specifically to the antigen. The equilibrium dissociation constant may be determined as known in the art. In the specific case of antibodies (Ab) binding to antigen (Ag), $K_d$ is the reciprocal of the affinity constant ($K_a$), which is defined as follows:

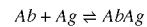

$$Ab + Ag \rightleftharpoons AbAg$$

$$K_a = \frac{[AbAg]}{[Ab][Ag]} = \frac{1}{K_d}$$

As used herein, the terms "treat," "treating" and "treatment" refer to the eradication, reduction or amelioration of symptoms of a disease or disorder, particularly, the eradication, removal, modification, or control of primary, regional, or metastatic cancer tissue that results from the administration of one or more therapeutic agents. In certain embodiments, such terms refer to the minimizing or delaying the spread of cancer resulting from the administration of one or more therapeutic agents to a subject with such a disease.

As used herein, the term "therapeutic agent" refers to any agent that can be used in the prevention, treatment, or management of a disease or disorder associated with overexpression of EphA2 and/or cell hyperproliferative diseases or disorders, particularly, cancer. In certain embodiments, the term "therapeutic agent" refers to cancer chemotherapeutics, radiation therapy, hormonal therapy, biological therapy/immunotherapy, and/or other forms of cancer treatment that can be used in conjunction with treatment with an EphA2 antibody.

As used herein, a "therapeutically effective amount" refers to that amount of the antibody sufficient to treat or manage a disease or disorder associated with EphA2 overexpression and/or cell hyperproliferative disease and, preferably, the amount sufficient to destroy, modify, control or remove primary, regional or metastatic cancer tissue. A therapeutically effective amount may refer to the amount of antibody sufficient to delay or minimize the onset of the hyperproliferative disease, e. g., delay or minimize the spread of cancer. A therapeutically effective amount may also refer to the amount of the antibody that provides a therapeutic benefit in the treatment or management of cancer. Further, a therapeutically effective amount with respect to an antibody means that amount of antibody alone, or in combination with other therapies, that provides a therapeutic benefit in the treatment or management of hyperproliferative disease or cancer. Used in connection with an amount of an EphA2 antibody, the term can encompass an amount that improves overall therapy, reduces or avoids unwanted effects, or enhances the therapeutic efficacy of or synergies with another therapeutic agent.

anti-EphA2 scFv Antibody

One aspect of the present application relates to a EphA2-specific human single-chain (anti-EphA2 scFv) antibody comprising an anti-EphA2 scFv domain. In some embodiments, the anti-EphA2 scFv antibody binds to EphA2 with 1:1 stoichiometry and has high specificity for EphA2 over other Eph receptors. In some embodiments, the anti-EphA2 scFv antibody blocks the binding of the biological ligands to EphA2 and thus, inactivates the receptor's natural functions in lymphoma cells. As a consequence, the antibody induces apoptosis and reduces cell proliferation in lymphoma cell lines. In some embodiments, the anti-EphA2 scFv antibody is an antibody comprising the amino acid sequence of SEQ ID. NO:1, 5, 6 or 7, or a functional variant thereof. In further embodiments, the anti-EphA2 scFv antibody comprises the amino acid sequence of SEQ ID. NO: 1, 5, 6 or 7. In further embodiments, the anti-EphA2 scFv antibody consists of the amino acid sequence of SEQ ID. NO:1, 5, 6 or 7.

Bispecific Anti-EphA2/Anti-CD20 Antibody

Another aspect of the present application relates to a fusion protein (a bispecific antibody) that comprises an anti-EphA2 antibody linked to an anti-CD20 antibody by a peptide linker. In some embodiments, the peptide linker is a short peptide of 5-25 amino acids and is rich in glycine for flexibility. CD20 is primarily found on the surface of immune system B cells. In some embodiments, the anti-CD20 antibody is rituximab, which is a chimeric monoclonal antibody against CD20. In some embodiments, the bispecific antibody comprises an anti-EphA2 scFv domain, an anti-CD20 scFv domain, and a peptide linker between the two domains. In some embodiment, the anti-EphA2/anti-CD20 bispecific antibody is an antibody comprising the amino acid sequence of SEQ ID. NO:1, 5, 6 or 7, or a functional variant thereof. In some embodiment, the anti-EphA2/anti-CD20 bispecific antibody is an antibody comprising the amino acid sequence of SEQ ID. NO:3 or a functional variant thereof. In some embodiment, the anti-EphA2/anti-CD20 bispecific antibody is an antibody comprising (1) the amino acid sequence of SEQ ID. NO:1, 5, 6 or 7 and (2) the amino acid sequence of SEQ ID NO: 3, or a functional variant thereof. In further embodiments, the anti-EphA2 bispecific antibody is an antibody comprising the amino acid sequence of SEQ ID NO:9 or a functional variant thereof.

In some embodiments, the anti-EphA2 scFv antibodies and anti-CD20/EphA2 scFv bispecific antibodies of the present application are subjected to further modification. The Modifications that may be performed in aspects of the application for the anti-EphA2 antibodies and anti-CD20/EphA2 scFv bispecific antibodies, include conversion of the scFv into Fab by attaching constant light domain and one constant heavy domain; and conversion of the Fab into full-length antibody by attaching an Fc region, i.e., attaching two more constant domains to the heavy chain and dimerizing the product covalently.

Polynucleotide

Another aspect of the present application relates to a nucleotide sequence that encodes the anti-EphA2/anti-CD20 bispecific antibody of the present application. In some embodiment, the nucleotide sequence comprises SEQ ID NO:8. Standard techniques known to those of skill in the art can be used to introduce mutations (e.g., additions, deletions, and/or substitutions) in the nucleotide sequence encoding a bispecific single chain anti-EphA2 antibody, including, for example, site-directed mutagenesis and PCR-mediated mutagenesis are routinely used to generate amino acid substitutions. In one embodiment, the nucleotide sequence encodes an amino acid sequence having less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions in relation to SEQ ID NO:9. In another embodiment, the nucleotide sequence encodes an amino acid sequence having conservative amino acid substitutions made at one or more predicted non-essential amino acid residues (i.e., amino acid residues which are not critical for the antibody to specifically bind to an Eph receptor) in relation to SEQ ID NO:9. Alternatively, mutations can be introduced randomly along all or part of the nucleotide sequence, such as by saturation mutagenesis. Following mutagenesis, the encoded antibody can be expressed and the activity of the antibody can be determined. In some embodiments, the anti-single-chain EphA2 antibody is encoded by an nucleotide sequence with at least about 45%, 50%, 60%, 70%, 80%, 90%, 95%, 98%, 99% identical to SEQ ID NO:8.

Expression Vectors

Another aspect of the present application relates to an expression vector that expresses the antibody or fusion antibody of the present application. A variety of host-expression vectors may be utilized to express the antibodies of the present application. In some embodiments, the expression vector is a bacteriophage vector, a plasmid vector, or a cosmid vector. In other embodiments, the expression vector is a viral vector. Such expression vector systems represent vehicles by which the antibodies of the present application may be produced in vitro and subsequently purified, as well as vehicles that are capable of transform or infect cells in vivo and express the antibodies of the present application in situ.

Examples of expression systems include, but are not limited to, microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody, are used for the expression of a recombinant antibody.

In bacterial systems, a number of expression vectors may be advantageously selected depending upon the use intended for the antibody being expressed. For example, when a large quantity of such a protein is to be produced, for the generation of pharmaceutical compositions of an antibody, vectors which direct the expression of high levels of fusion protein products that are readily purified may be desirable. Such vectors include, but are not limited to, pLK04 vector, pET32 vector, the *E. coli* expression vectors, in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. PGEX vectors may also be used to express foreign polypeptides as fusion proteins with glutathione 5-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody in infected hosts (e.g., see Logan & Shenk, 1984, *PNAS* 8 1:6355-6359). Specific initiation signals may also be required for efficient translation of insertedantibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, *Methods in Enzymol.* 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, W138, BT483, Hs578T, HTB2, BT20, NS1 and T47D, NS0 (a murine myeloma cell line that does not endogenously produce any immunoglobulin chains), CRL7030 and HsS78Bst cells.

The protein coding sequence in the expression vector of the present application is operably linked to one or more regulatory sequences that enable expression of the coded protein in a host cell. A nucleic acid sequence is "operably linked" to another nucleic acid sequence when the former is placed into a functional relationship with the latter. For example, a DNA for a presequence or signal peptide is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a signal peptide, contiguous and in reading phase. However, enhancers do not have to be contiguous. Linking is accomplished by ligation at convenient restriction sites. If such sites do not exist, synthetic oligonucleotide adaptors or linkers may be used in accordance with conventional practice. It will be appreciated by those skilled in the art that the design of the expression vector can depend on such factors as the choice of the host cell to be transformed, the level of expression of protein desired, and the like.

The above described "regulatory sequences" refer to DNA sequences necessary for the expression of an operably linked coding sequence in one or more host organisms. The term "regulatory sequences" is intended to include promoters, enhancers and other expression control elements (e.g., polyadenylation signals). Regulatory sequences include those which direct constitutive expression of a nucleotide sequence in many types of host cells or those which direct expression of the nucleotide sequence only in certain host cells (e.g., tissue-specific regulatory sequences). Expression vectors generally contain sequences for transcriptional termination, and may additionally contain one or more elements positively affecting mRNA stability.

The expression vector contains one or more transcriptional regulatory elements, including promoters and/or enhancers, for directing the expression of antibodies. A promoter comprises a DNA sequence that functions to initiate transcription from a relatively fixed location in regard to the transcription start site. A promoter contains core elements required for basic interaction of RNA polymerase and transcription factors, and may operate in conjunction with other upstream elements and response elements.

As used herein, the term "promoter" is to be taken in its broadest context and includes transcriptional regulatory elements (TREs) from genomic genes or chimeric TREs therefrom, including the TATA box or initiator element for accurate transcription initiation, with or without additional TREs (i.e., upstream activating sequences, transcription factor binding sites, enhancers, and silencers) which regulate activation or repression of genes operably linked thereto in response to developmental and/or external stimuli, and trans-acting regulatory proteins or nucleic acids. A promoter may contain a genomic fragment or it may contain a chimera of one or more TREs combined together.

Preferred promoters are those capable of directing expression in a target cell of interest. The promoters may include constitutive promoters (e.g., HCMV, SV40, elongation factor-1? (EF-1?)) or those exhibiting preferential expression in a particular cell type of interest. Enhancers generally refer to DNA sequences that function away from the transcription start site and can be either 5' or 3' to the transcription unit. Furthermore, enhancers can be within an intron as well as within the coding sequence. They are usually between 10 and 300 bp in length, and they function in cis. Enhancers function to increase and/or regulate transcription from nearby promoters. Preferred enhancers are those directing high-level expression in the exosome expressing cell.

The promoter and/or enhancer may be specifically activated either by light or specific chemical inducing agents. In some embodiments, inducible expression systems regulated by administration of tetracycline or dexamethasone, for example, may be used. In other embodiments, gene expression may be enhanced by exposure to radiation, including gamma irradiation and external beam radiotherapy (EBRT), or alkylating chemotherapeutic drugs.

Cell or tissue-specific transcriptional regulatory elements (TREs) can be incorporated into expression vectors to restrict expression to desired cell types. An expression vector may be designed to facilitate expression of the antibodies in one or more cell types.

In addition, the expression vectors may further include nucleic acid sequence encoding a reporter product or a selectable marker. A reporter product may be used to determine if the gene has been delivered to the cell and is being expressed. Exemplary marker genes include the *E. coli* lacZ gene, which encodes B galactosidase, and green fluorescent protein.

In some embodiments, the expression vector is a viral vector. A viral vectors may be derived from an adenovirus, adeno-associated virus (AAV), herpesvirus, vaccinia virus, poliovirus, poxvirus, a retrovirus (including a lentivirus, such as HIV-1 and HIV-2), Sindbis and other RNA viruses, alphavirus, astrovirus, coronavirus, orthomyxovirus, papovavirus, paramyxovirus, parvovirus, picornavirus, togaviruses and the like.

In some embodiments, the expression vector is a non-viral vector. A non-viral vector is simply a "naked" expression vector that is not packaged with virally derived components (e.g., capsids and/or envelopes), such as a plasmid vector, cosmid vector, phagemid vector or naked viral DNA.

In certain cases, the expression vectors may be engineered to target certain diseases and cell populations by using the targeting characteristics inherent to the virus vector or engineered into the virus vector. Specific cells may be "targeted" for delivery of polynucleotides, as well as expression. Thus, the term "targeting", in this case, may be based on the use of endogenous or heterologous binding agents in the form of capsids, envelope proteins, antibodies for delivery to specific cells, the use of tissue-specific regulatory elements for restricting expression to specific subset(s) of cells, or both.

Non-viral expression vectors can be utilized for non-viral gene transfer, either by direct injection of naked DNA or by encapsulating the antibody-encoding polynucleotides in liposomes, microparticles, microcapsules, virus-like particles, or erythrocyte ghosts. Such compositions can be further linked by chemical conjugation to, for example, microbial translocation domains and/or targeting domains to facilitate targeted delivery and/or entry of nucleic acids into the nucleus of desired cells to promote gene expression. In addition, plasmid vectors may be incubated with synthetic gene transfer molecules such as polymeric DNA-binding cations like polylysine, protamine, and albumin, and linked to cell targeting ligands such as asialoorosomucoid, insulin, galactose, lactose or transferrin.

Antibody-drug Conjugate

Another aspect of the present application relates to an antibody-drug conjugate comprising the anti-EphA2 antibody of the present application. In some embodiments, the anti-EphA2 antibody comprises an anti-EphA2 scFv domain. In some embodiments, the anti-EphA2 antibody comprises an anti-EphA2 scFv domain and an anti-CD20 scFv domain. One effective approach for enhancing the anti-tumor-potency of antibodies involves linking cytotoxic drugs or toxins to antibodies that are capable of being internalized by a target cell. These agents are termed antibody-drug conjugates (ADCs) and immunotoxins, respectively. Upon administration to a patient, ADCs and immunotoxins bind to target cells via their antibody portions and become internalized, allowing the drugs or toxins to exert their effect. In certain embodiments, the ADCs may be chemically modified (e.g., one or more chemical moieties can be attached to the antibody) or be modified to alter its glycosylation, again to alter one or more functional properties of the antibody. In certain embodiments, antibodies of the present invention or fragments or variants thereof are conjugated to a therapeutic agent such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Examples include paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

In particular embodiments antibodies may be fused to cyotoxic compounds, such as, auristatin, methotrexate, daunorubicin, Vinca alkaloids, mitomycin C, idarubicin, melphalan, doxorubicin, vinblastine, maytansinoids or calicheamicin by N- or C-terminal conjugation, using maleimidocaproyl, succinimide, hydrazide, cis-aconitate, thiocarbamoyl or other stable or cleavable linker. In certain embodiments, antibodies may be conjugated with lutenium-177, iodine-131 or other radiolabel for targeted radiation therapy. In other embodiments, antibodies may be fused with *Pseudomonas* exotoxin, *Staphylococcal* enterotoxin B, diphtheria toxin, tumor necrosis factor, interleukin-2, or their truncated mutants in order to create immunotoxic constructs.

In further embodiments, the cytotoxic agent is selected from the group consisting of an enediyne, a lexitropsin, a duocarmycin, a taxane, a puromycin, a dolastatin, a maytansinoid, and a *vinca* alkaloid. In other embodiments, the cytotoxic agent is paclitaxel, docetaxel, CC-1065, SN-38, topotecan, morpholino-doxorubicin, rhizoxin, cyanomorpholino-doxorubicin, dolastatin-10, echinomycin, combretastatin, calicheamicin, maytansine, DM-1, an auristatin or other dolastatin derivatives, such as auristatin E or auristatin F, AEB, AEVB, AEFP, MMAE (monomethylauristatin E), MMAF (monomethylauristatin F), eleutherobin or netropsin.

In still other embodiments, the cytotoxic agent is an anti-tubulin agent. In more specific embodiments, the cytotoxic agent is selected from the group consisting of a *vinca* alkaloid, a podophyllotoxin, a taxane, a baccatin derivative, a cryptophysin, a maytansinoid, a combretastatin, and a dolastatin. In more specific embodiments, the cytotoxic agent is vincristine, vinblastine, vindesine, vinorelbine, VP-16, camptothecin, paclitaxel, docetaxel, epithilone A, epithilone B, nocodazole, coichicine, colcimid, estramustine, cemadotin, discodermolide, maytansine, DM-1, an auristatin or other dolastatin derivatives, such as auristatin E or auristatin F, AEB, AEVB, AEFP, MMAE (monomethylauristatin E), MMAF (monomethylauristatin F), eleutherobin or netropsin.

Techniques for conjugating therapeutic moieties to antibodies are well known. Moieties can be conjugated to antibodies by any method known in the art, including, but not limited to aldehyde/Schiff linkage, sulphydryl linkage, acid-labile linkage, cis-aconityl linkage, hydrazone linkage, enzymatically degradable linkage. Additional techniques for conjugating therapeutic moieties to antibodies are well known. The fusion of an antibody to a moiety does not necessarily need to be direct, but may occur through linker sequences. Such linker molecules are commonly known in the art.

The linker may be an acid-labile hydrazone or hydrazide group that is hydrolyzed in the lysosome. In alternative embodiments, drugs can be appended to antibodies through other acid-labile linkers, such as cis-aconitic amides, orthoesters, acetals and ketals. Such linkers are relatively stable under neutral pH conditions, such as those in the blood, but are unstable at below pH 5, the approximate pH of the lysosome. In other embodiments, drugs are attached to the antibodies of the invention using peptide spacers that are cleaved by intracellular proteases. In yet other embodiments, the linker is a malonate linker, a maleimidobeiizoyl linker, or a 3'-N-amide analog. The choice and nature of the linker used is not limiting on the aspects of the application. In certain embodiments of the invention, the linker region between the drug moiety and the antibody moiety of the ADC is cleavable under certain conditions, wherein cleavage or hydrolysis of the linker releases the drug moiety from the antibody moiety. Preferably, the linker is sensitive to cleavage or hydrolysis under intracellular conditions.

Methods of Treating Proliferative Conditions

Another aspect of the present application relates to a method of treating a proliferative condition. In some embodiments, the method comprises the step of administering a therapeutically effective amount of an anti-EphA2 antibody to a subject in need thereof. In some embodiments, the anti-EphA2 antibody is an anti-EphA2 scFv antibody of the present application, or an anti-EphA2/anti-CD20 bispecific antibody of the present application, or an antibody-drug conjugate of the present application. In some embodiments, the proliferative condition is cancer. In some embodiments, the cancer is leukemia, lymphoma, carcinoma, sarcoma or melanoma. In some embodiments, the cancer is selected from the group consisting of lymphoma, leukemia, breast cancer, prostate cancer, pancreatic cancer, urinary bladder cancer, skin cancer, esophagus cancer, stomach cancer, lung cancer, ovarian cancer and brain cancer. In some embodiments, the cancer is lymphoma. In a particular embodiment, the lymphoma is follicular lymphoma. In some embodiments, the cancer is leukemia. In a particular embodiment, the leukemia is acute myelogenous leukemia (AML). In some embodiments, the anti-EphA2 scFv antibody comprises the amino acid sequence of SEQ ID NO: 1, 5, 6 or 7. In some embodiments, the anti-EphA2/anti-CD20 antibody comprises the amino acid sequence of SEQ ID NO:9.

In some embodiments, the method comprises the step of administering a therapeutically effective amount of an expression vector encoding the anti-EphA2 scFv antibody or the anti-EphA2/anti-CD20 bispecific antibody of the present application to a subject in need thereof, wherein the expression vector expresses the anti-EphA2 scFv antibody or the anti-EphA2/anti-CD20 bispecific antibody of the present application in the subject. In some embodiments, the expression vector is a plasmid vector. In other embodiments, the expression vector is a viral vector. The plasmid vector or viral vector may be introduce into a subject using methods known in the art.

In some embodiments, the expression vector is introduced into a cell in vitro to produce a recombinant cell which is then administered to the subject. Introduction of expression vector to the cell can be carried out by any method known in the art, including but not limited to, transfection, electroporation, microinjection, infection with a viral or bacteriophage vector containing the nucleic acid sequences, cell fusion, chromosome-mediated gene transfer, microcell mediated gene transfer, spheroplast fusion, etc. Numerous techniques are known in the art for the introduction of foreign genes into cells (see, e.g., Loeffler and Behr, 1993, Meth. Enzymol. 217: 599; Cohen et al., 1993, Meth. Enzymol. 217: 618) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny. The resulting recombinant cells can be delivered to a subject by various methods known in the art. The amount of cells envisioned for use depends on the desired effect, patient state, etc., and can be determined by one skilled in the art.

Alternatively, naked DNA may be employed. Uptake efficiency of naked DNA may be improved by compaction or by using biodegradable latex beads. Such delivery may be improved further by treating the beads to increase hydrophobicity and thereby facilitate disruption of the endosome and release of the DNA into the cytoplasm.

Cells for treatment can originate from a variety of different sources, including the breast, prostrate, lung, brain, colon, bladder, kidney, cervix, testis, ovary, liver, pancreas, head and neck, anogenital tissue, adrenal gland, and blood. The present methods may be applied to any patient (e.g., a human of any age, gender, or ethnicity) who has been diagnosed with cancer. This includes patients diagnosed with a breast cancer; a biliary tract cancer; a bladder cancer; a brain cancer (e.g., a glioblastomas or medulloblastomas); a cervical cancer; a choriocarcinoma; a colon cancer; an endometrial cancer; an esophageal cancer; a gastric cancer; a hematological neoplasm (e.g., acute lymphocytic leukemia or lymphoma, Hodgkin's disease, acute myelogenous leukemia, T-cell acute lymphoblastic leukemia/lymphoma, hairy cell leukemia, chronic lymphocytic leukemia, chronic myelogenous leukemia, multiple myeloma, or an adult T-cell leukemia/lymphoma); an intraepithelial neoplasm including Bowen's disease and Paget's disease; a liver cancer; a lung cancer; a neuroblastoma; a melanoma, an oral cancer including squamous cell carcinoma; an ovarian cancer including ovarian cancer arising from epithelial cells, stromal cells, germ cells and mesenchymal cells; a pancreatic cancer; a prostate cancer; a rectal cancer; a sarcoma, including angiosarcoma, gastrointestinal stromal tumors, leiomyosarcoma, rhabdomyosarcoma, liposarcoma, fibrosarcoma, and osteosarcoma; a renal cancer including renal cell carcinoma and Wilms tumor; a skin cancer including basal cell carcinoma and squamous cell cancer; a testicular cancer including germinal tumors such as seminoma, non-seminoma (teratomas, choriocarcinomas), stromal tumors, and germ cell tumors; and a thyroid cancer including thyroid adenocarcinoma and medullary carcinoma.

Cancers related to the overexpression of EphA2 include those of the immune system (lymphoma, leukemia); breast (cancer-derived cell lines Hs578T, MDA-435, MDA-231 and BT549); prostate (cancer-derived cell line PC3); pancreas (cancer-derived cell lines PANC 1, MIAPaCa2); urinary bladder (cancer-derived cell lines T24, TCCSUP, UMUC-3); skin (cancer-derived cell lines C8161, MUM-2B); esophagus (cancer-derived cell line TE1); stomach (cancer-derived cell lines AGS, SGC-7901); lung (cancer-derived cell lines MMC-1, MMC-2, MMC-3); ovary (cancer-derived cell lines SKOV3, EG, 222, HeyA8); brain (cancer-derived cell lines A172MG, DBTRG-5MG, U-251MG).

Combination Therapies for Cancer

In an aspect of the application, there are provided methods for treating cancer by administering one or more compositions of the single-chain anti-EphA2 antibody in combination with any other treatment or to patients who have proven refractory to other treatments but are no longer on these treatments. In certain embodiments, the patients being treated by the single-chain anti-EphA2 antibody are patients already being treated with chemotherapy, radiation therapy, hormonal therapy, or biological therapy/immunotherapy. Among these patients are refractory patients and those with cancer despite treatment with existing cancer therapies. In other embodiments, the patients have been treated and have no disease activity and one or more compositions of the invention are administered to prevent the recurrence of cancer.

In certain embodiments, the existing treatment is chemotherapy. In particular embodiments, the existing treatment includes administration of chemotherapies including, but not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, docetaxel, etc. Among these patients are patients treated with radiation therapy, hormonal therapy and/or biological therapy/immunotherapy. Also among these patients are those who have undergone surgery for the treatment of cancer.

Alternatively, the invention also encompasses methods for treating patients undergoing or having undergone radiation therapy. Among these are patients being treated or previously treated with chemotherapy, hormonal therapy and/or biological therapy/immunotherapy. Also among these patients are those who have undergone surgery for the treatment of cancer.

Methods of Treating Conditions Relating to Overexpressing EphA2

Another aspect of the present application relates to a method for treating a condition that is related to overexpression of EphA2. In some embodiments, the method comprises the step of administering a therapeutically effective amount of an anti-EphA2 antibody to a subject in need thereof. In some embodiments, the anti-EphA2 antibody is an anti-EphA2 scFv antibody of the present application, or an anti-EphA2/anti-CD20 bispecific antibody of the present application, or an antibody-drug conjugate of the present application. In some embodiments, the method comprises the step of administering a therapeutically effective amount of an expression vector encoding the anti-EphA2 scFv antibody or the anti-EphA2/anti-CD20 bispecific antibody of the present application to a subject in need thereof, wherein the expression vector expresses the anti-EphA2 scFv antibody or the anti-EphA2/anti-CD20 bispecific antibody of the present application in the subject.

In some embodiments, the condition that is related to overexpression of EphA2 is a pre-cancerous condition associated with cells that overexpress EphA2. Administration of the an anti-EphA2 scFv antibody of the present application or an anti-EphA2/anti-CD20 bispecific antibody of the present application decrease the likelihood that the pre-cancerous condition progresses to malignant cancer. In some embodiments, the pre-cancerous condition is high-grade prostatic intraepithelial neoplasia (PIN), fibroadenoma of the breast, fibrocystic disease, or compound nevi.

In some embodiments, the condition that is related to overexpression of EphA2 is a non-cancerous condition. Examples of such condition include, but are not limited to, asthma, chronic obstructive pulmonary disorder (COPD), restenosis (smooth muscle and/or endothelial), psoriasis, cataract, pathological retinal angiogenesis, acute kidney injury (renal ischemia-reperfusion injury, IRI), bone remodeling diseases, mammary gland morphogenesis defects, inner ear development defects, myocardial infarction, atherosclerosis, and other cardiovascular diseases and inflammatory syndromes.

Formulations

Another aspects of the present application relates to compositions comprising the anti-EphA2 scFv antibody of the present application, the anti-EphA2/anti-CD20 bispecific antibody of the present application, the antibody-drug conjugate of the present application, or expression vectors of the present application. In some embodiments, the compositions are bulk drug compositions useful in the manufacture of pharmaceutical compositions (e. g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of an antibody and/or therapeutic agent or a combination of those agents and a pharmaceutically acceptable carrier. In one embodiment, the compositions comprise a therapeutically effective amount of the anti-EphA2 scFv antibody, the anti-EphA2/anti-CD20 bispecific antibody, the antibody-drug conjugate or expression vectors of the present application, and a pharmaceutically acceptable carrier. In a further embodiment, the composition of the invention further comprises an additional therapeutic, e. g., anti-cancer, agent.

In a specific embodiment, the term "pharmaceutically acceptable" means approved by a regulatory agency of the Federal or a state government or listed in the U. S. Pharmacopeia or other generally recognized pharmacopeia for use in animals, and more particularly in humans. The term "carrier" refers to a diluent, adjuvant (e.g., Freund's adjuvant (complete and incomplete) or, more preferably, MF59C. 1 adjuvant available from Chiron, Emeryville, Calif.), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the single-chain anti-EphA2 antibody are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Administration

The compositions of the present application can be formulated as neutral or salt forms Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Various delivery systems are known and can be used to administer a single chain anti-EphA2 antibody or the combination of a single chain anti-EphA2 antibody and a therapeutic agent useful for preventing or treating cancer, e. g., encapsulation in liposomes, microparticles, microcapsules, recombinant cells capable of expressing the antibody or antibody fragment, receptor-mediated endocytosis, construction of a nucleic acid as part of a retroviral or other vector, etc. Methods of administering a single chain anti-EphA2 antibody invention include, but are not limited to, parenteral administration (e. g., intradermal, intramuscular, intraperitoneal, intravenous and subcutaneous), epidural, and mucosal (e. g., intranasal, inhaled, and oral routes). In a specific embodiment, a single chain anti-EphA2 antibody are administered intramuscularly, intravenously, or subcutaneously. A single chain anti-EphA2 antibody may be administered by any convenient route, for example by infusion or bolus injection, by absorption through epithelial or mucocutaneous linings (e. g., oral mucosa, rectal and intestinal mucosa, etc.) and may be administered together with other biologically active agents. Administration can be systemic or local. In a specific embodiment, it may be desirable to administer the anti-EphA2 scFv antibodies, the anti-EphA2/anti-CD20 bispecific antibodies, the antibody-drug conjugates, or expression vectors of the present application locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers.

Any suitable route or mode of administration can be employed for providing the patient with a therapeutically or prophylactically effective dose of the fusion protein or expression vector. Exemplary routes or modes of administration include parenteral (e.g., intravenous, intraarterial, intramuscular, subcutaneous, intratumoral), oral, topical (nasal, transdermal, intradermal or intraocular), mucosal (e.g., nasal, sublingual, buccal, rectal, vaginal), inhalation, intralymphatic, intraspinal, intracranial, intraperitoneal, intratracheal, intravesical, intrathecal, enteral, intrapulmonary, intralymphatic, intracavital, intraorbital, intracapsular and transurethral, as well as local delivery by catheter or stent.

A pharmaceutical composition comprising an antibody or expression vector in accordance with the present disclosure may be formulated in any pharmaceutically acceptable carrier(s) or excipient(s). As used herein, the term "pharmaceutically acceptable carrier" includes any and all solvents, dispersion media, coatings, antibacterial and antifungal agents, isotonic and absorption delaying agents, and the like that are physiologically compatible. Pharmaceutical compositions may comprise suitable solid or gel phase carriers or excipients. Exemplary carriers or excipients include but are not limited to, calcium carbonate, calcium phosphate, various sugars, starches, cellulose derivatives, gelatin, and polymers such as polyethylene glycols. Exemplary pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the therapeutic agents.

The antibodies or recombinant expression vectors can be incorporated into a pharmaceutical composition suitable for parenteral administration. Suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

Therapeutic antibody preparations can be lyophilized and stored as sterile powders, preferably under vacuum, and then reconstituted in bacteriostatic water (containing, for example, benzyl alcohol preservative) or in sterile water prior to injection. Pharmaceutical composition may be formulated for parenteral administration by injection e.g., by bolus injection or continuous infusion.

The therapeutic agents in the pharmaceutical compositions may be formulated in a "therapeutically effective amount". A "therapeutically effective amount" or "effective amount" refers to an amount effective, at dosages and for periods of time necessary, to achieve the desired therapeutic result. A therapeutically effective amount of the recombinant vector may vary depending on the condition to be treated, the severity and course of the condition, the mode of administration, whether the antibody or agent is administered for preventive or therapeutic purposes, the bioavailability of the particular agent(s), the ability of the fusion protein or vector to elicit a desired response in the individual, previous therapy, the age, weight and sex of the patient, the patient's clinical history and response to the antibody, the type of the fusion protein or expression vector used, discretion of the attending physician, etc. A therapeutically effective amount is also one in which any toxic or detrimental effects of the recombinant vector is outweighed by the therapeutically beneficial effects.

Preferably, the polypeptide domains in the fusion protein or polynucleotide are derived from the same host in which they are to be administered in order to reduce inflammatory responses against the administered therapeutic agents.

The fusion protein or expression vector is suitably administered to the patent at one time or over a series of treatments and may be administered to the patient at any time from diagnosis onwards. The fusion protein or expression vector may be administered as the sole treatment or in conjunction with other drugs or therapies useful in treating the condition in question.

Dosage

The appropriate dosage ("therapeutically effective amount") of the antibodies will depend, for example, on the severity and course of the cancer being treated, the mode of administration, the bioavailability of the therapeutic agent(s), previous therap(ies), the age and weight of the patient, the patient's clinical history and response to the antibodies, the type of antibody used, discretion of the attending physician, etc. A "therapeutically effective amount" refers to an amount effective, at dosages and for periods of time necessary, to achieve the desired therapeutic result. A therapeutically effective amount of the recombinant vector may vary depending on the condition to be treated, the severity and course of the condition, the mode of administration, whether the antibody or agent is administered for preventive or therapeutic purposes, the bioavailability of the particular agent(s), the ability of the fusion protein or vector to elicit a desired response in the individual, previous therapy, the age, weight and sex of the patient, the patient's clinical history and response to the antibody, the type of the fusion protein or expression vector used, discretion of the attending physician, etc. A therapeutically effective amount is also one in which any toxic or detrimental effects of the recombinant vector is outweighed by the therapeutically beneficial effects.

The antibodies are suitably administered to the patent at one time or over a series of treatments and may be administered to the patient at any time from diagnosis onwards. The antibodies may be administered as the sole treatment or in combination with other drugs or therapies useful in treating cancer. When used with other drugs, the antibodies may be used at a lower dose to reduce toxicities and/or side effects.

Dosages can be tested in several art-accepted animal models suitable for a particular cancer, autoimmmune disease or alloimmune response.

The antibodies may be administered to the patient with known methods, such as intravenous administration as a bolus or by continuous infusion over a period of time, by intramuscular, intraperitoneal, intracerebrospinal, subcutaneous, intra-articular, intrasynovial, intrathecal, oral, topical and/or inhalation routes. As a general proposition, the therapeutically effective amount(s) of the above described antibodies will be in the range of about 1 ng/kg body weight/day to about 100 mg/kg body weight/day whether by one or more administrations. In a particular embodiments, each therapeutic agent is administered in the range of from about 1 ng/kg body weight/day to about 10 mg/kg body weight/day, about 1 ng/kg body weight/day to about 1 mg/kg body weight/day, about 1 ng/kg body weight/day to about 100 μg/kg body weight/day, about 1 ng/kg body weight/day to about 10 μg/kg body weight/day, about 1 ng/kg body weight/day to about 1 μg/kg body weight/day, about 1 ng/kg body weight/day to about 100 ng/kg body weight/day, about 1 ng/kg body weight/day to about 10 ng/kg body weight/day, about 10 ng/kg body weight/day to about 100 mg/kg body weight/day, about 10 ng/kg body weight/day to about 10 mg/kg body weight/day, about 10 ng/kg body weight/day to about 1 mg/kg body weight/day, about 10 ng/kg body weight/day to about 100 μg/kg body weight/day, about 10 ng/kg body weight/day to about 10 μg/kg body weight/day, about 10 ng/kg body weight/day to about 1 μg/kg body weight/day, 10 ng/kg body weight/day to about 100 ng/kg body weight/day, about 100 ng/kg body weight/day to about 100 mg/kg body weight/day, about 100 ng/kg body weight/day to about 10 mg/kg body weight/day, about 100 ng/kg body weight/day to about 1 mg/kg body weight/day, about 100 ng/kg body weight/day to about 100 μg/kg body weight/day, about 100 ng/kg body weight/day to about 10 μg/kg body weight/day, about 100 ng/kg body weight/day to about 1 μg/kg body weight/day, about 1 μg/kg body weight/day to about 100 mg/kg body weight/day, about 1 μg/kg body weight/day to about 10 mg/kg body weight/day, about 1 μg/kg body weight/day to about 1 mg/kg body weight/day, about 1 μg/kg body weight/day to about 100 μg/kg body weight/day, about 1 μg/kg body weight/day to about 10 μg/kg body weight/day, about 10 μg/kg body weight/day to about 100 mg/kg body weight/day, about 10 μg/kg body weight/day to about 10 mg/kg body weight/day, about 10 μg/kg body weight/day to about 1 mg/kg body weight/day, about 10 μg/kg body weight/day to about 100 μg/kg body weight/day, about 100 μg/kg body weight/day to about 100 mg/kg body weight/day, about 100 μg/kg body weight/day to about 10 mg/kg body weight/day, about 100 μg/kg body weight/day to about 1 mg/kg body weight/day to about 100 mg/kg body weight/day, about 1 mg/kg body weight/day to about 10 mg/kg body weight/day, about 10 mg/kg body weight/day to about 100 mg/kg body weight/day.

In certain embodiments, the antibodies are administered at a dose of 500 μg to 20 g every three days, or 10 μg to 400 mg/kg body weight every three days. In other embodiments, the antibodies are administered in the range of about 10 ng to about 100 ng per individual administration, about 10 ng to about 1 μg per individual administration, about 10 ng to about 10 μg per individual administration, about 10 ng to about 100 μg per individual administration, about 10 ng to about 1 mg per individual administration, about 10 ng to about 10 mg per individual administration, about 10 ng to about 100 mg per individual administration, about 10 ng to about 1000 mg per injection, about 10 ng to about 10,000 mg per individual administration, about 100 ng to about 1 μg per individual administration, about 100 ng to about 10 μg per individual administration, about 100 ng to about 100 μg per individual administration, about 100 ng to about 1 mg per individual administration, about 100 ng to about 10 mg per individual administration, about 100 ng to about 100 mg per individual administration, about 100 ng to about 1000 mg per injection, about 100 ng to about 10,000 mg per individual administration, about 1 μg to about 10 μg per individual administration, about 1 μg to about 100 μg per individual administration, about 1 μg to about 1 mg per individual administration, about 1 μg to about 10 mg per individual administration, about 1 μg to about 100 mg per individual administration, about 1 μg to about 1000 mg per injection, about 1 μg to about 10,000 mg per individual administration, about 10 μg to about 100 μg per individual administration, about 10 μg to about 1 mg per individual administration, about 10 μg to about 10 mg per individual administration, about 10 μg to about 100 mg per individual administration, about 10 μg to about 1000 mg per injection, about 10 μg to about 10,000 mg per individual administration, about 100 μg to about 1 mg per individual administration, about 100 µg to about 10 mg per individual administration, about 100 µg to about 100 mg per individual administration, about 100 µg to about 1000 mg per injection, about 100 µg to about 10,000 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1000 mg per injection, about 10 mg to about 10,000 mg per individual administration, about 100 mg to about 1000 mg per injection, about 100 mg to about 10,000 mg per individual administration and about 1000 mg to about 10,000 mg per individual administration. The antibodies may be administered daily, or every 2, 3, 4, 5, 6 and 7 days, or every 1, 2, 3 or 4 weeks.

In other particular embodiments, the antibodies are administered at a dose of about 0.0006 mg/day, 0.001 mg/day, 0.003 mg/day, 0.006 mg/day, 0.01 mg/day, 0.03 mg/day, 0.06 mg/day, 0.1 mg/day, 0.3 mg/day, 0.6 mg/day, 1 mg/day, 3 mg/day, 6 mg/day, 10 mg/day, 30 mg/day, 60 mg/day, 100 mg/day, 300 mg/day, 600 mg/day, 1000 mg/day, 2000 mg/day, 5000 mg/day or 10,000 mg/day. As expected, the dosage(s) will be dependent on the condition, size, age and condition of the patient.

In certain embodiments, the pharmaceutical composition comprises an effective amount of the recombinant virus, such as rAAV, in an amount comprising at least $10^{10}$, at least $10^{11}$, at least $10^{12}$, at least $10^{13}$, or at least $10^{14}$ genome copies (GC) or recombinant viral particles per kg, or any range thereof. In certain embodiments, the pharmaceutical composition comprises an effective amount of the recombinant virus, such as rAAV, in an amount comprising at least $10^{10}$, at least $10^{11}$, at least $10^{12}$, at least $10^{13}$, at least $10^{14}$, at least $10^{15}$ genome copies or recombinant viral particles genome copies per subject, or any range thereof.

Kits

Another aspect of the present application relates to a pharmaceutical pack or kit comprising one or more containers filled with a an anti-EphA2 scFv antibody, an anti-EphA2/anti-CD20 bispecific antibody, an antibody-drug conjugate, or an expression vectors of the present application. Additionally, one or more other therapeutic agents useful for the treatment of a cancer or a condition related to overexpression of EphA2 can also be included in the pharmaceutical pack or kit. Another embodiment also provides a pharmaceutical pack or kit comprising one or more containers filled with one or more of the ingredients of the pharmaceutical compositions. Optionally associated with such container (s) can be a notice in the form prescribed by a governmental agency regulating the manufacture, use or sale of pharmaceuticals or biological products, which notice reflects approval by the agency of manufacture, use or sale for human administration.

Various alternatives (e.g., different types of cancers and types of reagents) may be utilized. It is to be understood that various combinations can be employed and any one or more of the listed alternatives can be excluded from the compositions of the invention. The contents of all references, patents and published patent applications cited throughout this application, as well as the Figures and Tables are incorporated herein by reference. Below are disclosed methods of generating and characterizing single-chain anti-EphA2 antibodies. Further aspects and advantages of the application will appear from the following description taken together with the accompanying drawings. One of ordinary skill will understand that the following examples are not limiting on aspects of the application.

EXAMPLES

Example 1

Materials and Methods

Phage display selections for the production of anti-EphA2 scFv. The ligand-binding domain of EphA2 was expressed in 293-HEK cells as Fc-fusion and purified by ProteinA-Sepharose affinity and Superdex-200 size exclusion-chromatography as described earlier (Himanen J P, Goldgur Y, Miao H, Myshkin E, Guo H, Buck M, et al. Ligand recognition by A-class Eph receptors: crystal structures of the EphA2 ligand-binding domain and the EphA2/ephrin-A1 complex. EMBO Rep. 2009; 10:722-8). The EphA2 specific binders were selected by phage display from synthetic single-chain antibody fragment (scFv) phage libraries ScFvM and ScFvP (Brockmann E C, Akter S, Savukoski T, Huovinen T, Lehmusvuori A, Leivo J, et al. Synthetic single-framework antibody library integrated with rapid affinity maturation by VL shuffling. Protein engineering, design & selection: PEDS. 2011; 24:691-700.). The methods used for M13 phage display have been described in Huovinen T, Syrjanpaa M, Sanmark H, Brockmann E C, Azhayev A, Wang Q, et al. Two ScFv antibody libraries derived from identical VL-VH framework with different binding site designs display distinct binding profiles. Protein engineering, design & selection: PEDS. 2013; 26:683-93. Purified recombinant EphA2 was first immobilized on Dynabeads® M-270 Epoxy (Life Technologies Inc.) using 20 µg of antigen per mg of beads, according to the instructions of the Dynabeads® Antibody Coupling Kit. Phosphate buffered saline (PBS), supplemented with 0.05% n-Dodecyl β-D-maltoside (DDM) and 0.01% Cholesterol Hemisuccinate (CHS), was used for the last washing step and to resuspend the beads. At the first selection round $10^{12}$ colony-forming units (cfu) of each of the two scFv phage libraries were used as mixed and at the second round the phage input was $10^{11}$ cfu from the first round output. The mass of antigen-coupled beads used for the first and second round selections was 0.5 mg or 0.05 mg, respectively. The phages were incubated with the beads in TBS (50 mM Tris, 150 mM NaCl, 1% BSA, pH7.5) containing 0.05% DDM and 1% bovine serum albumin (BSA) for 30-60 minutes at room temperature with rotation. The unbound phages were removed by washing twice with the same buffer, followed by one wash with TBS+0.02% NaN3+0.05% Tween-20. Elution of the bound phages was performed with trypsin.

Enrichment of specific phages was monitored by a phage immunoassay as described in ref. Huovinen T, Syrjanpaa M, Sanmark H, Brockmann E C, Azhayev A, Wang Q, et al. Two ScFv antibody libraries derived from identical VL-VH framework with different binding site designs display distinct binding profiles. Protein engineering, design & selection: PEDS. 2013; 26:683-93. The plates (Maxisorp, Nunc) were coated with antigen by incubating a saturating amount of EphA2 in 0.1M NaH2PO4 at +35° C., o/n. The wells were washed twice and blocked with 50 mM NaH2PO4, 0.1% Germall II, 6% Sorbitol, 1% milk by incubating at room temperature for 2 h.

ELISA screening. After two rounds of phage display selection, the scFvs genes were cut off from the phagemid vector by SfiI digestion and cloned as a pool into the vector pEB06H for single-clone immunoactivity screening Huovinen T, Syrjanpaa M, Sanmark H, Brockmann E C, Azhayev A, Wang Q, et al. Two ScFv antibody libraries derived from identical VL-VH framework with different binding site designs display distinct binding profiles. Protein engineering, design & selection: PEDS. 2013; 26:683-93. In this vector, the scFv is fused to the gene encoding for bacterial alkaline phosphatase (AP). Electro-competent *E. coli* XL 1-Blue cells (Stratagene) were transformed, and scFv-AP fusion protein was expressed in a 96-well format. The activity of antibody fragments was determined on EphA2 coated Maxisorp plates by ELISA as described in Paino A, Ahlstrand T, Nuutila J, Navickaite I, Lahti M, Tuominen H, et al. Identification of a novel bacterial outer membrane interleukin-1Beta-binding protein from Aggregatibacter *actinomycetemcomitans*. PLoS One. 2013; 8:e70509. As a cross reactivity control the assay was also performed on plates coated with EphB2ECD-Fc fusion protein.

Cloning of FLAG-tagged scFv constructs. The genes originating from the human synthetic scFv antibody library (pEB06H/scFv vector; Brockmann E C, Akter S, Savukoski T, Huovinen T, Lehmusvuori A, Leivo J, et al. Synthetic single-framework antibody library integrated with rapid affinity maturation by VL shuffling. Protein engineering, design & selection: PEDS. 2011; 24:691-700.), and encoding EphA2-specific scFv antibodies were expressed as fusions to alkaline phosphatase (AP). The gene cassette in this vector has the following orientation: SfiI (restriction enzyme site)-scFv-SfiI/AvaI-AP-Histidine tag-STOP codon-HindIII. By virtue of the construction, the scFv genes can easily be switched between appropriate vectors using SfiI enzyme to maintain the cloning frame and the gene orientation. Due to high background staining in COS-7 cells by several anti-AP antibodies that were tested, scFv genes were subcloned into newly synthesized vector (His-FLAG-pEB06) as a scFv-His-FLAG fusion. NsiI-(SfiI)-HindIII fragment was removed from the pEB06H backbone vector, and a new synthetic gene cassette containing NsiI-SfiI/AvaI-TEVPro (protease cleavage site)-His6-Gly-Ser-Gly-linker-FLAG-STOP-HindIII was inserted in-frame into pEB06H to create His-FLAG-pEB06 (GeneArt Gene Synthesis, Life Technologies). The EphA2-encoding scFv genes were subcloned into SfiI/AvaI-digested His-FLAG-pEB06, and the construct was checked by restriction site mapping. ScFv antibodies were expressed in bacteria, purified using HisSpinTrap (GE Healthcare) columns, and used to detect Eph receptor expression on COS-7 cells by confocal microscopy.

Production of monomeric anti-EphA2 sc-Fv for crystallization: The scFv-AP fusion protein, described above, is a dimer as AP is a homodimer. To produce monomeric scFv for crystallization experiments, the D2 scFv was cloned into the pEB04 vector with Sfi-digestion. This construct generates scFv with a C-terminal His-tag. The scFv-6×His protein was expressed in *E. coli* (AD494) and purified on a Chelating Sepharose (GE Healthcare) column according to manufacturer's instructions.

Pull-down assay. Pull-down experiment was performed as described earlier Himanen J P, Chumley M J, Lackmann M, Li C, Barton W A, Jeffrey P D, et al. Repelling class discrimination: ephrin-A5 binds to and activates EphB2 receptor signaling. Nat Neurosci. 2004; 7:501-9. In short, 10 g of the ligand-binding or extracellular domains of Eph receptors were incubated with the D2 scFv at room temperature for 30 minutes in Hepes-buffered saline, Protein-A Sepharose beads (GE Healtcare) were added and mixed for 30 minutes. The harvested beads were washed and the bound proteins were separated on a 5-20% PAGE gels (BioRad). The stoichiometry of the receptor/antibody binding was evaluated by size exclusion chromatography. The proteins were diluted to 0.5 mg/ml, applied on a Superdex-200 10/300 column (Pharmacia), then mixed in a uni-molar ratio and run again.

Cell cultivation, transfection and imaging. COS-7 (African green monkey kidney fibroblast-like; ATCC CRL-1651) cells were cultivated in DMEM (Dulbecco's modified eagle) medium supplemented with 10% fetal calf serum, 4 mM glutamine and 100 U/ml Pen/Strep antibiotics at +37° C. Cells cultivated on glass slides were transfected at 90% confluency with pDT101 expression vector encoding full-length human EphA2 protein, or with myc-FLAG-tagged vector encoding human EphA7 (hEphA7) (RC226293, Origene). Transfections were performed with Fugene6 (Promega) transfection reagent according to manufacturer's instructions. Transfected and control (non-transfected) cells were incubated at 37° C. for 24 h before fixation (4% formalin in PBS) and permeabilization (when applicable; 0.1% Triton-X100 in PBS). Antibody staining was performed at room temperature. Overexpression of FLAG-tagged hEphA7 was visualized in permeabilized cells using anti-FLAG antibodies. Binding of anti-EphA2 scFv antibodies to overexpressed EphA2 and EphA7 receptors was detected by rabbit anti-DYKDDDDK (FLAG) Tag Antibody (#2368, Cell Signaling Technology) in non-permeabilized cells. As controls, commercial rabbit anti-EphA2 and rat anti-EphA7 (Santa Cruz) were used in similar manner. Primary antibody binding was visualized by secondary mouse/rabbit/rat Alexa Fluor (AF) 488/568-labeled antibodies when applicable. All antibodies were diluted in PBS supplemented with 3% BSA. The wells were incubated at RT for 1.5 h in the presence of primary antibodies, after which the cells were washed three times with PBS and AF-conjugated secondary antibodies were added. After 30 min incubation at RT, the cells were washed and nuclei stained with DAPI. Fixed, permeabilized and immunostained cells were then mounted on microscope slides in Mowiol 4-88 (Calbiochem-Novabiochem), 25% glycerol, 0.1 M Tris-HCl, pH 8.5, containing 25 mg/ml Dabco (Sigma-Aldrich) and examined with Zeiss LSM780 confocal microscope using a Plan-Apochromat objective (63× oil). The images were processed with BioImageXD Kankaanpaa P, Paavolainen L, Tiitta S, Karjalainen M, Paivarinne J, Nieminen J, et al. BioImageXD: an open, general-purpose and high-throughput image-processing platform. Nature methods. 2012; 9:683-9.

Lymphoma cell culture and apoptosis assays. Lymphoma cell lines Raji, Ly-19, and Toledo were maintained in RPMI 1640 with 10% fetal bovine serum, 1% L-Glutamine and 1% penicillin/streptomycin. Human lymphoma cell lines treated with single-chain anti-EphA2 antibody were analyzed for cell viability and cell proliferation assays. Briefly, cells were seed at 5×10^4 per mL and they were treated with single-chain anti-EphA2 antibody. After 24 h, 48 h and 72 h of treatment cell apoptosis and proliferation was assessed using were count using Guava ViaCount (cat. 4000-0041).

Crystallization and data collection: For crystallization, the D2 scFv antibody was mixed with the ligand-binding domain of EphA2 in a unimolar ratio and the complex was purified on a Superdex-200 HiLoad 16/80 (GE Helathcare) column. The EphA2/D2 complex was dialyzed against 5 mM HEPES (pH 7.2), 10 mM KCl, 2 mM MgCl2 and concentrated to 10 mg/ml. It was crystallized in a hanging drop against 20 mM Citrate (pH 5.6), 200 mM Ammonium Sulfate, 20% PEG 4,000. The crystals were flash frozen and data was collected at APS (Argonne National Laboratory, Chicago) beamline ID-24. The structure was determined by molecular replacement with the EphA2/ephrin-A1 structure (PDB ID: 3HEI) as a search template using CCP4/Amore Collaborative Computational Project N. The CCP4 suite: programs for protein crystallography. Acta crystallographica Section D, Biological crystallography. 1994; 50:760-3. and the model was built and refined in Refmac, followed by an iterative process in CNS Brunger A T, Adams P D, Clore G M, DeLano W L, Gros P, Grosse-Kunstleve R W, et al. Crystallography & NMR system: A new software suite for macromolecular structure determination. Acta crystallographica Section D, Biological crystallography. 1998; 54:905-21.

Example 2

Library Screening for EphA2 Binders

Two rounds of phage display selection were performed to enrich EphA2-specific binders from the mixture of the synthetic antibody libraries scFvP and scFvM Brockmann E C, Akter S, Savukoski T, Huovinen T, Lehmusvuori A, Leivo J, et al. Synthetic single-framework antibody library integrated with rapid affinity maturation by VL shuffling. Protein engineering, design & selection: PEDS. 2011; 24:691-700; Huovinen T, Syrjanpaa M, Sanmark H, Brockmann E C, Azhayev A, Wang Q, et al. Two ScFv antibody libraries derived from identical VL-VH framework with different binding site designs display distinct binding profiles. Protein engineering, design & selection: PEDS. 2013; 26:683-93. Phage immunoassay gave a signal-to-background ratio of 22 for the phage pool after the second round indicating clear enrichment of EphA2-binding phages. The scFv genes from the second round were cloned into the pEB06H vector to express soluble scFv-alkaline phosphatase fusion proteins for activity screening. ELISA-based screening of 96 individual clones yielded 58 EphA2-positive clones (sg/bg>3). None of the clones showed cross reactivity to the EphB2-Fc control protein. The EphA2-binding activity was confirmed with a secondary screening assay. Sequencing of 12 clones revealed 6 unique binders. One of the unique binders, 'D2', was selected for further studies. Its sequence is shown in Table 1.

Example 3

Biochemical Characterization of the D2 scFv

Pull-down assays were carried out to evaluate the interactions of the ligand-binding or extracellular domains of different Eph receptors with the D2 scFv. Antibodies derived from the synthetic libraries scFvM and scFvP have capability to interact with Protein-A as the human VH3-family variable domain is employed as a part of framework of the libraries. This interaction was used to pull-down untagged Eph receptors (FIG. 1, Panel A). The results confirmed the binding specificity of the D2 for EphA2. As shown in FIG. 1, Panel A, the D2 scFv pulls down untagged EphA2, but not EphB2 or EphA7. The full extracellular domain of EphA7 was used to verify that there are no nonspecific epitopes outside the Eph ligand-binding domain.

Figure 1B:
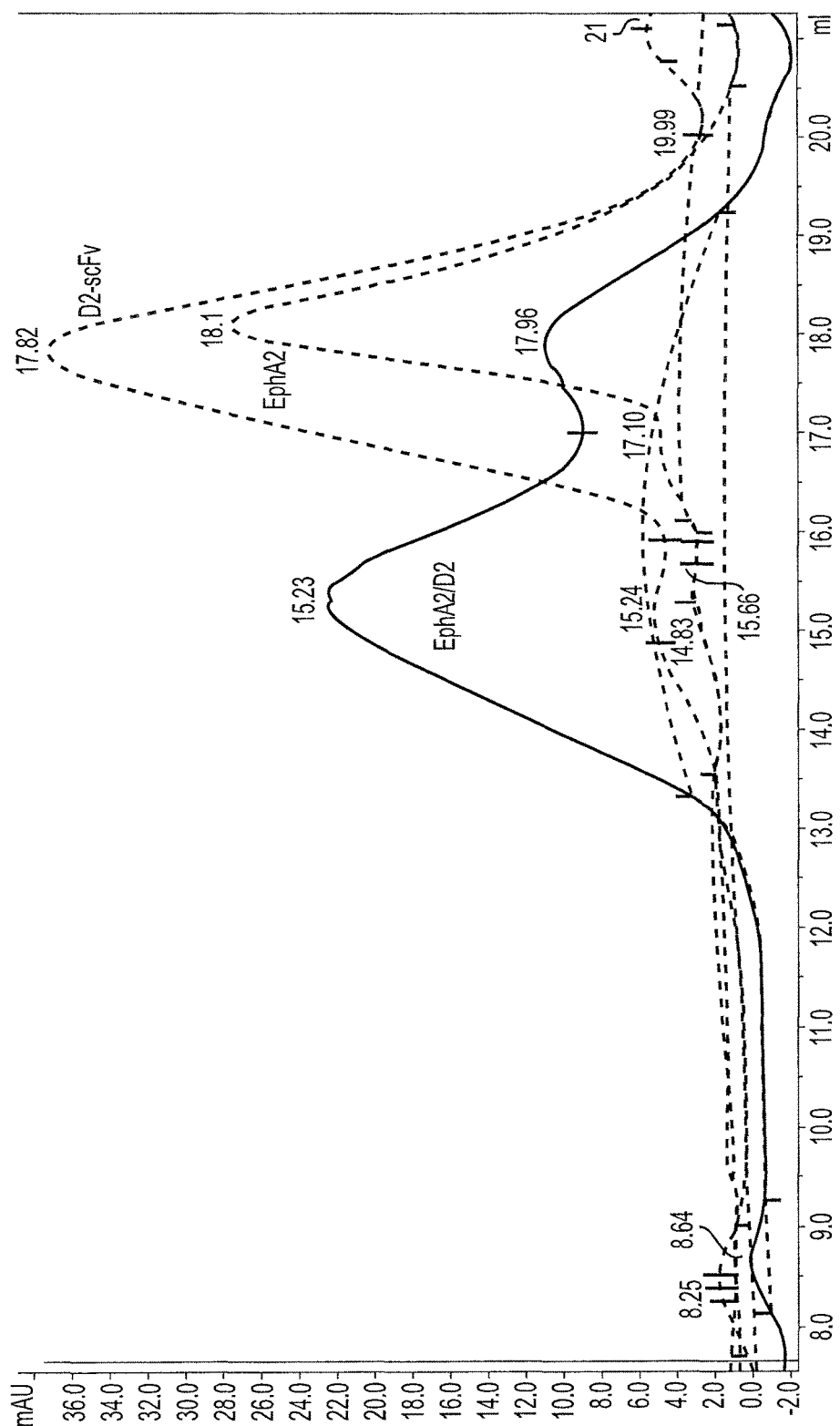
FIG. 1B is a diagram showing the size-exclusion chromatography of the D2-scFv/EphA2 complex. Monomeric EphA2 and D2 both run close to the 23 kDa molecular weight marker on Superdex-200 (17.8 ml and 18.1 ml, respectively). The peak of their complex shifts to 15.2 ml, indicating a formation of a 1:1 heterodimer, since 67 kDa molecular weight marker runs at 14.3 ml.

Size-exclusion chromatography was performed to evaluate the stoichiometry of the D2-scFv/EphA2 complex. As seen in FIG. 1B, both EphA2 and D2 run around 17-18 ml on a Superdex column, close to the 23 kDa molecular weight marker. After mixing, the complex runs at 15.2 ml as compared to 14.3 ml for the 67 kDa marker. Thus, in size-exclusion chromatography, the D2-scFv/EphA2 complex appears as a 1:1 heterodimer.

Example 4

The D2 scFv Binds to EphA2 but not EphA7 on COS-7 Cells

Figure 2:
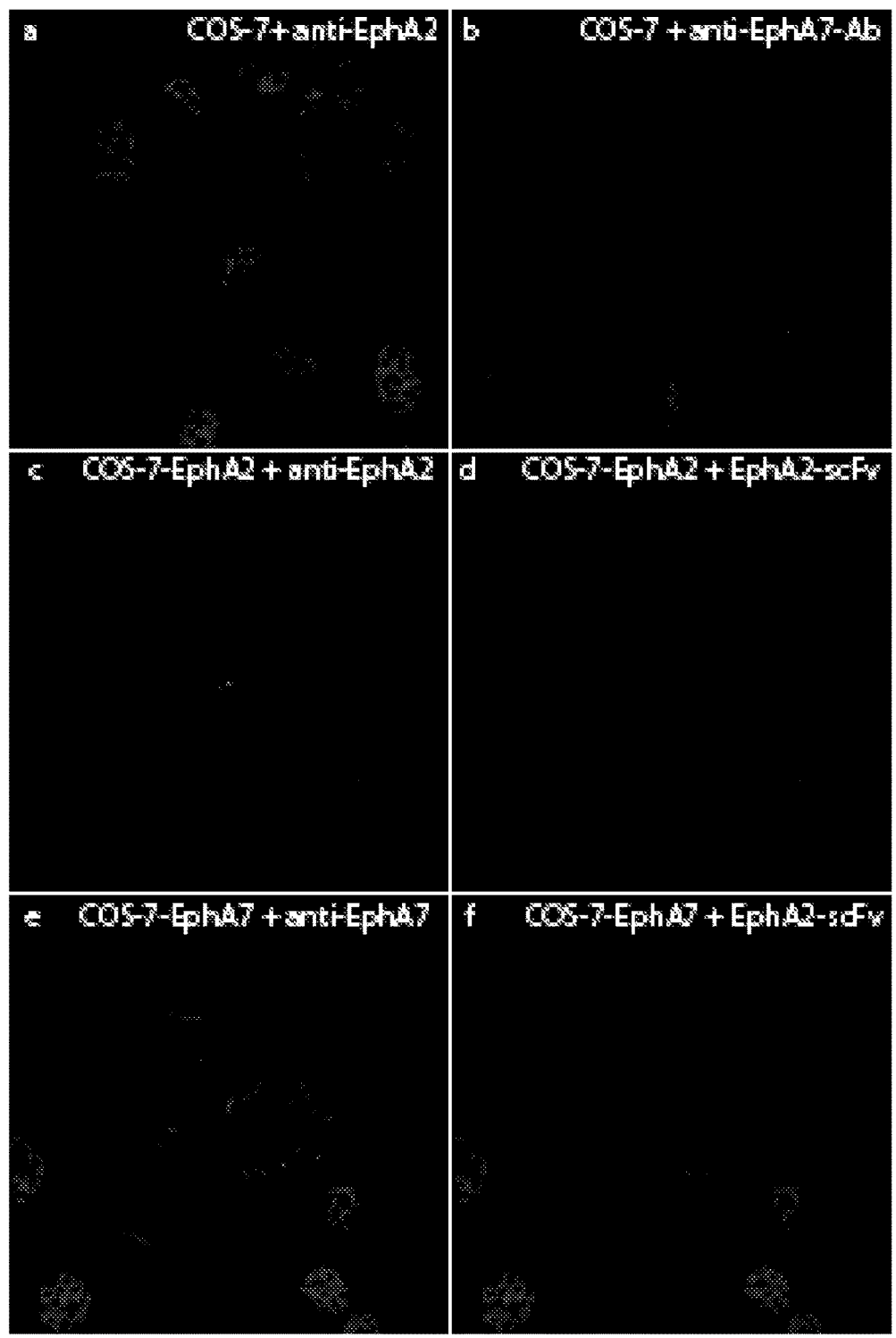
FIG. 2 is a composite of pictures showing reactivities of EphA2-specific scFv antibodies to COS-7 cell lines overexpressing EphA2 and EphA7 receptors. COS-7 cells were transfected with constructs overexpressing EphA2 and EphA7 receptors. The receptors on the surface of non-permeabilized cells were detected by type-specific (FIG. 2C and FIG. 2E) and scFv (FIG. 2D and FIG. 2F) antibodies, respectively. Antibody-binding was visualized by secondary Alexa Fluor 488/568 antibodies. Lack of background staining by the antibodies is shown in FIG. 2A and FIG. 2B.

In order to verify the specific binding of D2 in cell culture, COS-7 cells were transfected with plasmids bearing full-length EphA2 or EphA7. Overexpression of the gene products were verified by commercial antibodies. FIG. 2, Panels A and B indicate lack of background staining by these antibodies, while EphA2 and EphA7 were detected in the overexpressing cells (Panels C and E, respectively). Importantly, the D2 scFv detected EphA2 but not EphA7 in COS-7 cells (Panels D and F), demonstrating the specificity of D2 to the EphA2 receptor.

TABLE 1

Amino acid sequence of the anti-EphA2 scFv antibody D2, shown in the order of variable light chain/linker/variable heavy chain (SEQ ID NO: 1). The linker region is bold underlined. Amino acid residues in the EphA2/D2 interface are shown in enlarged bold italics. (See also FIG. 3B)

| | | |
|---|---|---|
| 1 | eivltqspgtlslspgeratlscrasqsvsssnlawyqqkpgqaprlli*y* | 50 |
| 51 | gassra*t*gvpdrfsgsgsgtdftltisrlepedfavyycqqsssypwtfg | 100 |
| 101 | qgtkveikrtggggsgaggsggggtggggsevqllesgggglvqpggslrl | 150 |
| 151 | scaasgf*t*fs*r*ywmhwvrqapgkglewvssisp*y*dgetnyadsvkgrfti | 200 |
| 201 | srdnskntlylqmnslraedtavyycarise*wynw*aydvfdywgqgtlvt | 250 |
| 251 | vss | 253 |

Example 5

Crystal Structure of the D2/EphA2 Complex

Figure 3A:
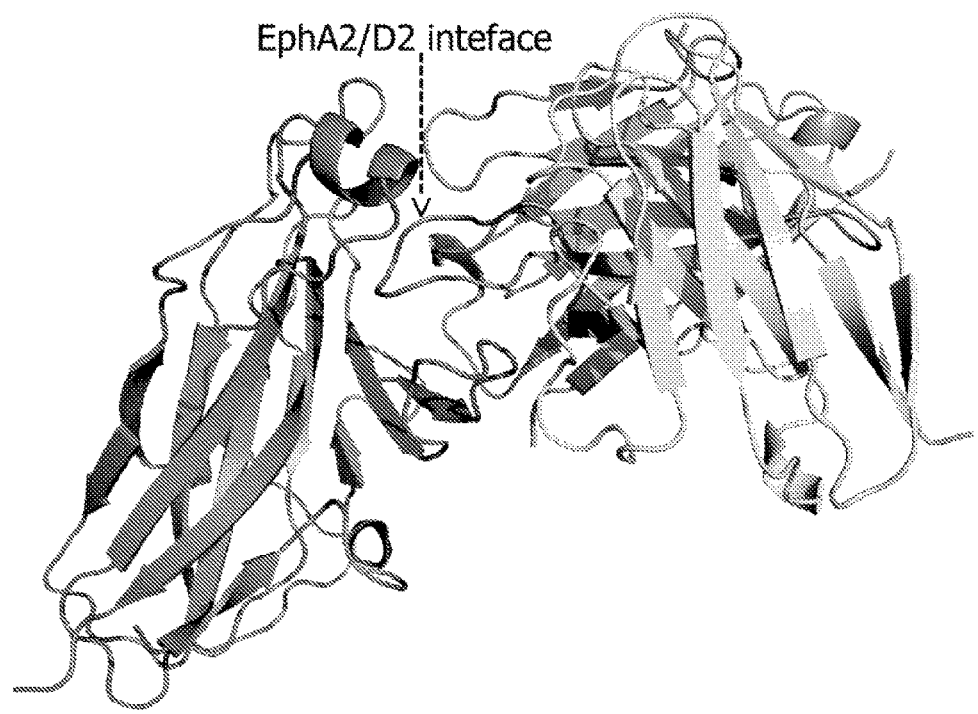
FIG. 3A shows overall structure of the EphA2/D2-scFv receptor/antibody complex. The scFv variable light chain is the structure on the right at the foreground of the diagram, the variable heavy chain is the structure on the right in the background of the diagram, and the EphA2 receptor is the structure on the left of the diagram. The EphA2/D2 interface mediates antigen recognition and specificity.
Figure 3B:
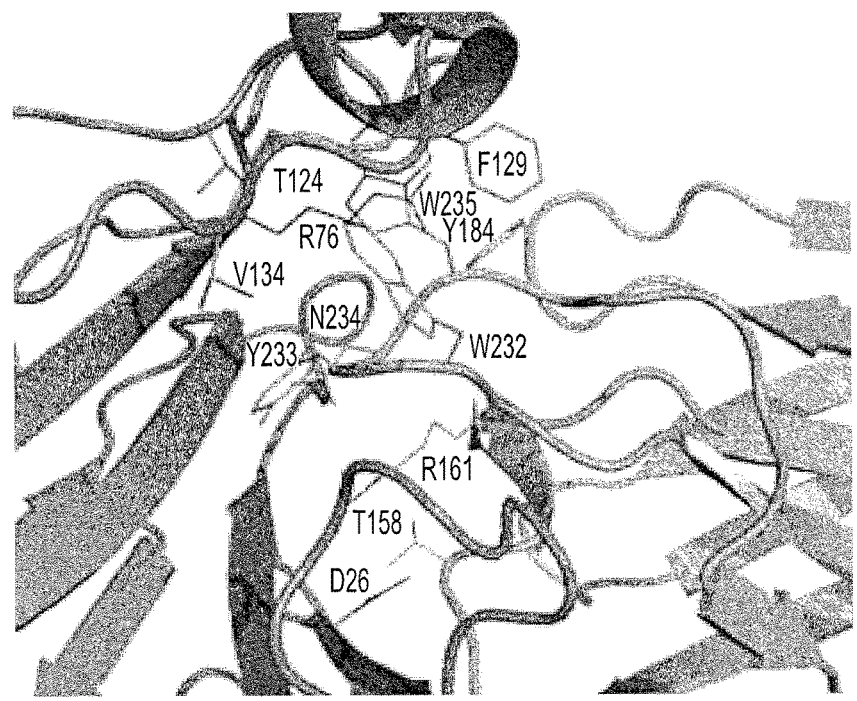
FIG. 3B shows interacting amino acid residues in the interface between the EphA2 receptor (left structure) and D2-scFv antibody (right structure). Most of the interacting residues are hydrophobic and reside within the CDR-H3 loop of the scFv heavy chain, a common feature for majority of the known antibodies-antigen complexes.

The high-resolution crystal structure of the complex was determined between the D2 scFv antibody and the EphA2 ligand-binding domain (LBD; FIG. 3A). The model is refined at 2.5 Å resolution and has an R-factor of 20.7%. As all immunoglobulin variable domains, Bhat T N, Bentley G A, Fischmann T O, Boulot G, Poljak R J. Small rearrangements in structures of Fv and Fab fragments of antibody D1.3 on antigen binding. Nature. 1990; 347:483-5; Zdanov A, Li Y, Bundle D R, Deng S J, MacKenzie C R, Narang S A, et al. Structure of a single-chain antibody variable domain (Fv) fragment complexed with a carbohydrate antigen at 1.7-A resolution. Proc Natl Acad Sci USA. 1994; 91:6423-7, the variable-light and variable-heavy chains of D2 have two antiparallel beta-sheets each, one consisting of four and the other of five beta-stands. In addition, the heavy chain has two short alpha helices. The beta-strands are connected with loops of varying length, including a 16-amino acids long CDR3 in the heavy chain that appears as the main determinant for the specificity of D2 (see below), as well as five shorter CDR-loops. The twenty amino acid linker, connecting the C-terminus of VL to the N-terminus of VH, is unstructured and is not visible in the electron density map. Crystallographic statistics are presented in Table 2.

TABLE 2

Data collection and refinement statistics. (Values in the brackets are for the highest resolution shell.)

| | |
|---|---|
| Wavelength (Å) | 0.9792 |
| Resolution range (Å) | 30 – 2.4 (2.5/2.46* – 2.4) |
| Space group | $P4_12_12$ |
| Cell dimensions | a = b = 87.77 Å, c = 239.88 Å |
| Redundancy | 7.2 (7.3) |
| Completeness | 99.9 (100.0) |
| $R_{sym}$ | 0.057 (0.432) |
| $I/\sigma_I$ | 18.5 (2.5) |
| Subunits/ASU | 2 |
| Reflections total | 35740 (2702) |
| Working set | 33860 (2566) |
| Test set | 1880 (136) |
| $R_{work}/R_{free}$ | 0.207/0.255 (0.328/0.366) |
| Number of atoms | 6683 |
| Protein | 6840 |
| Water | 290 |
| Ion | 10 |
| Mean B value (Å$^2$) | 40.1 |
| RMS deviations: | |
| Bond lengths (Å) | 0.013 |
| Bond angles (°) | 1.753 |
| Ramachandran Analysis: | |
| Favored | 95.7 |
| Allowed | 4.3 |
| Disallowed | 0 |

*Resolution limits for data integration and refinement statics, respectively.

The structure of the EphA2 receptor in the complex is remarkably similar to that in its complex with the ephrin-A1 ligand Himanen J P, Goldgur Y, Miao H, Myshkin E, Guo H, Buck M, et al. Ligand recognition by A-class Eph receptors: crystal structures of the EphA2 ligand-binding domain and the EphA2/ephrin-A1 complex. EMBO Rep. 2009; 10:722-8. The two EphA2 structures can be superimposed with root-mean-square deviation (r.m.s.d.) between Ca positions of about 1.0 Å. The only important difference is the D-E loop that is shifted towards the center of the hydrophobic cavity on the surface of the receptor (see also FIG. 3, Panel C). This conformational re-arrangement allows Met32 of the EphA2 to form a Van der Waals bond with the Trp232 of the D2 antibody. Another small difference between the structures lies within the A-C loop of the EphA2, but this structural element is too far from the D2/EphA2 interface to have any influence on the antigen/antibody binding or specificity.

Figure 3C:
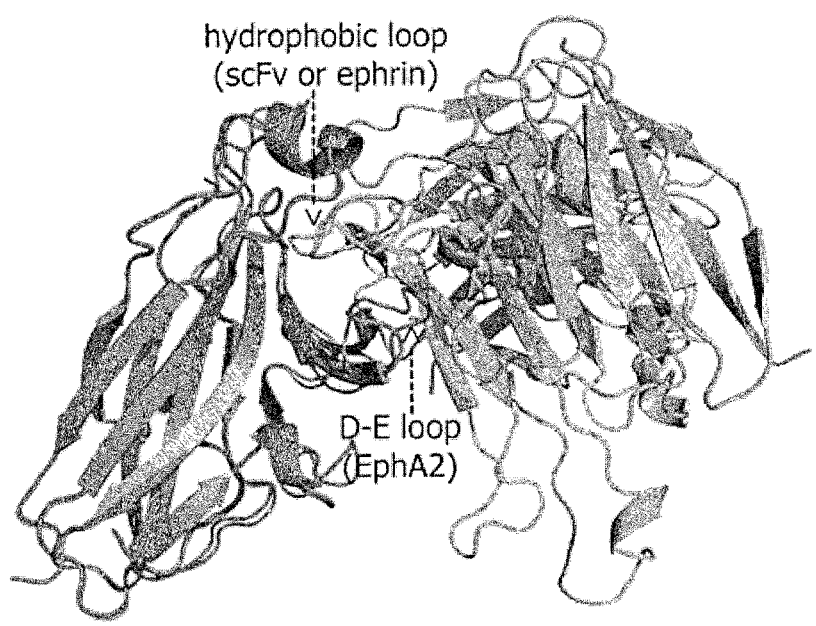
FIG. 3C shows superimposition of the ligand-binding domain of EphA2 bound to either the D2-scFv antibody (right structure top) or ephrin-A1 (right structure bottom). EphA2 in complex with scFv is shown on the left of the diagram and in complex with ephrin (darker structure on the right in the diagram). The large protein-protein interfaces centers around the same hydrophobic loop (scFv or ephrin) and cavity (receptor) in both structures. The structure of EphA2 in both complexes is very similar; the only important difference is the D-E loop that is shifted towards the center of the EphA2 hydrophobic surface cavity when in complex with scFv.

There are two 1:1 EphA2/D2 complexes in the asymmetric unit of the crystals. Both complexes have a nearly identical, extensive EphA2/D2 interaction interface, stretching over 1,300 Å2 on each molecule. The interface has a fairly broad network of hydrogen and Van der Waals bonds and salt bridges that stabilize the complex. The interacting amino acid residues in the interface are shown in FIG. 3, Panel B and Table 1. The majority of the contact-forming residues of scFv reside in the three complementarity determining regions (CDR) of the heavy chain, and only two light chain amino acids in the CDR-2 region directly interact with the antigen. Hence, the heavy chain clearly plays a prominent role in the defining the specificity of D2 to EphA2. Especially the CDR-H3 loop of the heavy chain is tightly interacting with several residues of EphA2. The central role of CDR-H3 in the binding is a common feature for the majority of the known antibodies-antigen complexes Rock E P, Sibbald P R, Davis M M, Chien Y H. CDR3 length in antigen-specific immune receptors. The Journal of experimental medicine. 1994; 179:323-8.

The two EphA2/D2 heterodimers in the asymmetric unit pack via another small EphA2/D2 crystal-packing interface (burying approximately 450 Å2 on each molecule). This interface has only three D2 residues that are in direct contact with the EphA2 receptor. They are all outside of the CDR loops and 13-19 Å apart from each other and thus, not able to form a continuous binding surface.

Example 6

D2 scFv Competes with Ephrin-A5 for EphA2 Binding

Interestingly, the high-affinity, interface between EphA2 and D2 centers around the exact same hydrophobic Eph surface cavity as the interface between EphA2 and ephrin-A1 (Himanen J P, Goldgur Y, Miao H, Myshkin E, Guo H, Buck M, et al. Ligand recognition by A-class Eph receptors: crystal structures of the EphA2 ligand-binding domain and the EphA2/ephrin-A1 complex. EMBO Rep. 2009; 10:722-8; FIG. 3, Panel C). The apex of the lengthy CDR-H3 in D2 protrudes deep into the ligand-binding cavity of EphA2. At the very tip of the loop there are four consecutive residues, W232, Y233, N234, and W235, the side chain of which point into different directions. These residues constitute an anchor-like structure that occupies the ligand-binding pocket forming multiple contacts with the antigen. The three bulky hydrophobic residues on the tip of CDR-H3 are well suited to interact with the hydrophobic ligand-binding cavity of the EphA2 in a way similar to the ephrin G-H loops in the known Eph/ephrin complexes Himanen J P, Goldgur Y, Miao H, Myshkin E, Guo H, Buck M, et al. Ligand recognition by A-class Eph receptors: crystal structures of the EphA2 ligand-binding domain and the EphA2/ephrin-A1 complex. EMBO Rep. 2009; 10:722-8; Himanen J P, Rajashankar K R, Lackmann M, Cowan C A, Henkemeyer M, Nikolov D B. Crystal structure of an Eph receptor-ephrin complex. Nature. 2001; 414:933-8. Thus, Thr124, Phe129, and V134 of EphA2 form a hydrophobic contact area for the CDR-H3 anchor, consisting of W232, Y233, and W235, while a hydrogen bond between Arg76 (EphA2) and Tyr184 (scFv) further stabilize the complex. It is interesting to note that while the sequence similarity is very high between different members of the Eph family, a careful assessment of the sequences provides an explanation for the D2 scFv specificity. Indeed, although the Arg76 is conserved throughout the family, the interface residues T124, F129, and V134 are evolutionary somewhat diverged: Thr-124 is Phe, Phe-129 is Leu, and Val-134 is Met in both EphB2 and EphA7. These subtle differences might, in part, account for the high specificity of D2 scFv for EphA2.

Figure 4:
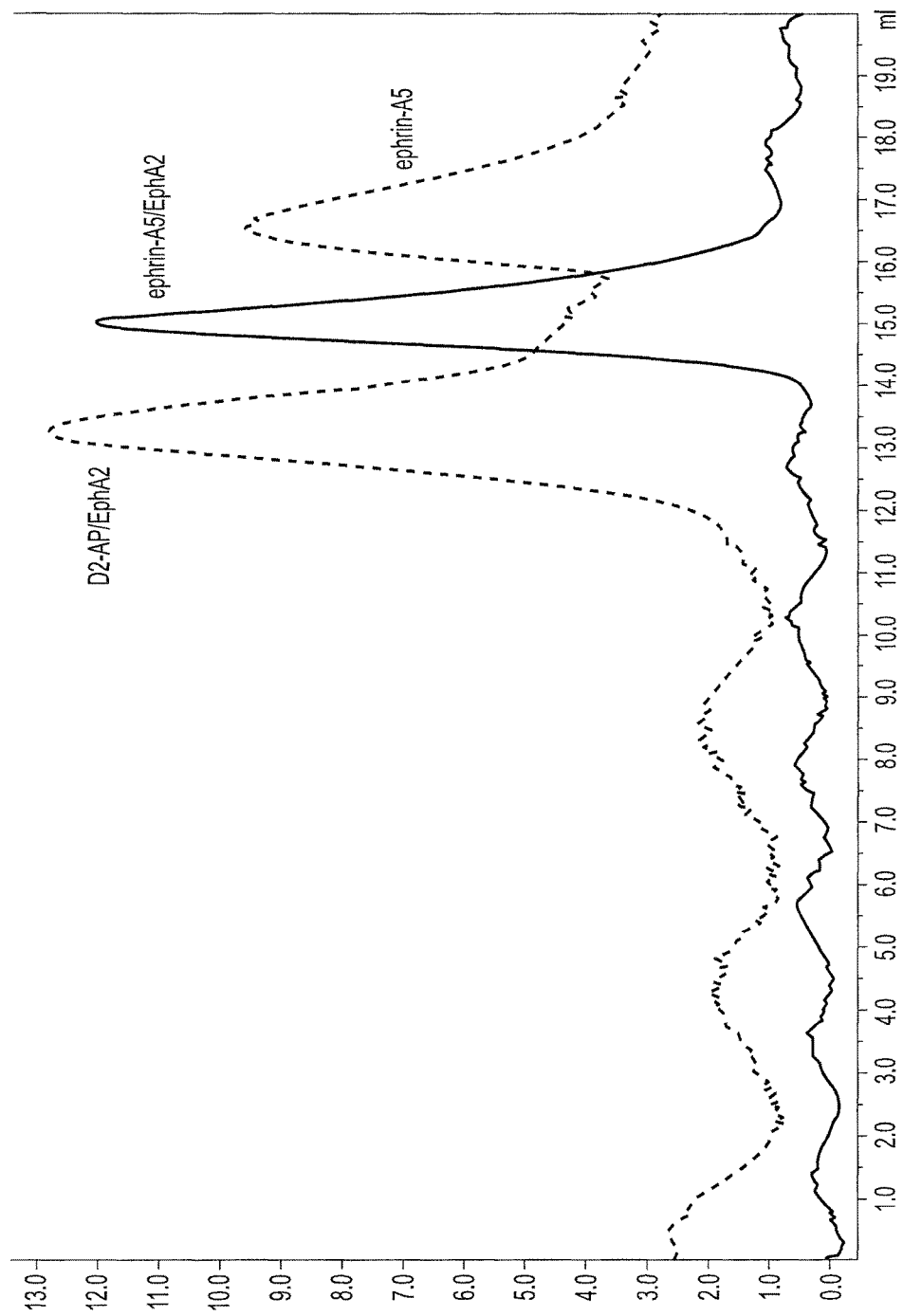
FIG. 4 is a diagram showing D2-scFv blocks the binding of ephrin-A5 to its EphA2 receptor. When added to a D2-scFv/EphA2 complex, ephrin-A5 runs as a monomer on a size exclusion column but forms a heterodimeric receptor/ligand complex when mixed with an un-complexed EphA2.

To evaluate the potential consequence of the apparently overlapping binding epitopes, the influence of D2-scFv was measured on the binding of EphA2 with its ephrin ligand. As expected from the structure, the scFv antibody upon binding to EphA2 blocks the binding of ephrin-A5 to the receptor. As shown in FIG. 4, ephrin-A5 runs as a monomeric ligand on a size exclusion column when added to a preformed EphA2/D2 complex. However, when mixed with the un-complexed EphA2, ephrin-A5 forms a heterodimeric receptor/ligand complex that runs near the position of the 43 kDa molecular marker.

Example 7

Effect of EphA2-scFv on Lymphoma Cells

Figure 5:
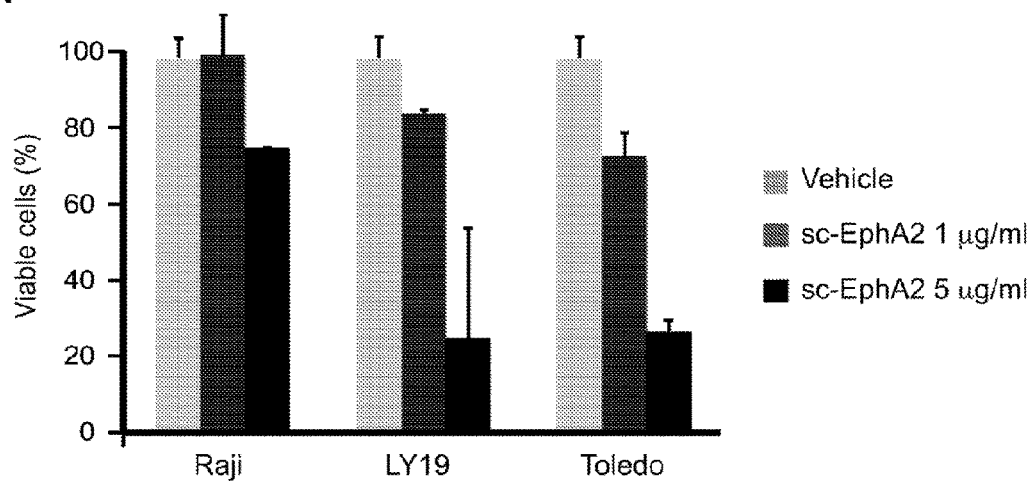
FIG. 5 is a diagram showing that exogenous administration of anti-EphA2 scFv antibody reduces cell proliferation and induces apoptosis in lymphoma cell lines.
Figure 5:
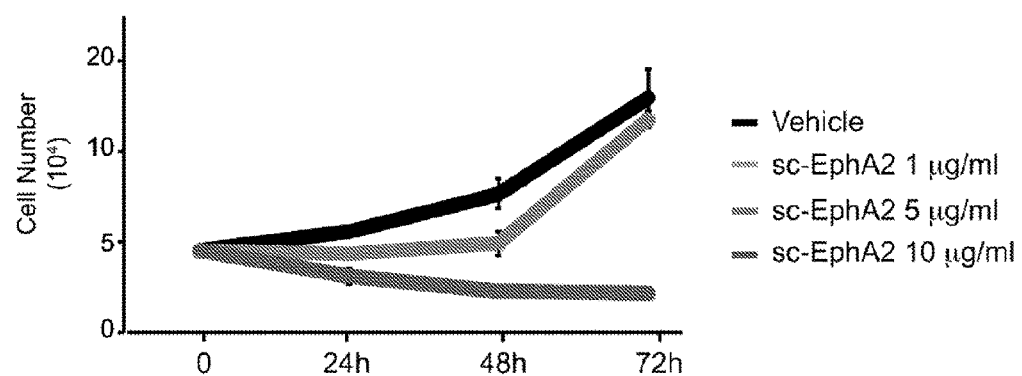
Figure 6:
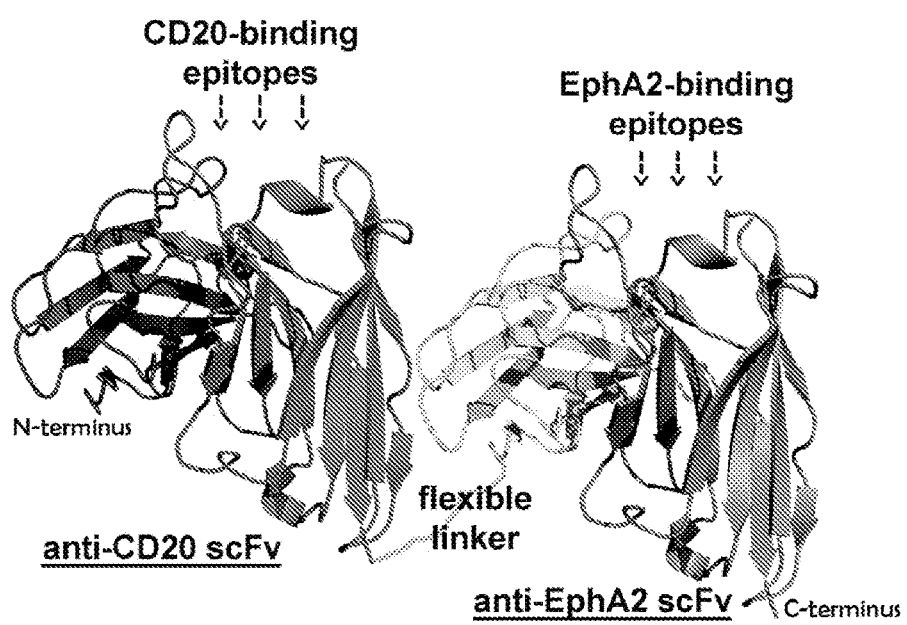
FIG. 6 is a diagram showing the overall structure of the anti-EphA2-anti-CD20 bispecific antibody.

Finally, we tested the effect of D2 scFv on lymphoma cell cultures (FIG. 5). Lymphoma cell lines express EphA2, the activity of which can be regulated by a soluble form of EphA7 Oricchio E, Nanjangud G, Wolfe A L, Schatz J H, Mavrakis K J, Jiang M, et al. The Eph-receptor A7 is a soluble tumor suppressor for follicular lymphoma. Cell. 2011; 147:554-64. The EphA2-scFv antibody was used as an alternative way to block EphA2 activity in lymphoma. Treatment with the EphA2 single-chain antibody indeed induces apoptosis (FIG. 5, Panel A) and reduces cell proliferation (FIG. 5, Panel B) in the lymphoma cells lines.

Example 8

Effect of EphA2-scFv on Leukemia Cells

Cell surface expression of EphA2 was examined using flow cytometry in peripheral blood (PB), bone marrow (BM) and leukopheresis samples from patients with acute myelogenous leukemia (AML). Thirty primary AML samples were screened with diverse clinical and mutation characteristics that include 6 FLT3-ITD, 2 DNMT3A, 1 TET2, and 1 p53 mutant samples. The expression of EphA2 was assessed using multi-parameter flow cytometry using the lymphoma cell line (Raji) as a positive control, as it has been reported to express EphA2. The expression of EphA2 was evaluated under culture conditions as well as without culture. Out of the 30 samples tested prior to culture 73.3% expressed greater than 90% EphA2 relative to isotype control. The mean cell surface expression of EphA2 in blasts was 91.6% (ranging from: 43.7%-100%) with a mean fluorescence intensity (MFI) of 141.1 (ranging from: 7.0-352.0; MFI of 5.6 for isotype control). Interestingly, post-culture, an increase in EphA2 expression was observed, bringing the total percent of samples expressing more than 90% EphA2 to 86.6%. In addition to the increase of samples expressing high levels of EphA2 post-culture, the average mean fluorescence intensity (MFI) of the cohort also increased from the non-cultured samples. The mean cell surface expression of EphA2 in blasts was 95.4% (ranging from: 64.4%-99.7%) with a mean fluorescence intensity (MFI) of 201.5 (18.4-675.0; MFI of 4.4 for isotype control). Furthermore, a more significant increase was seen in the CD34+ population and little to no change in the CD34- population. These data show that many AML primary samples express EphA2, and that culturing with cytokines can provide samples with a significant overall increase in EphA2 expression.

Figure 7:
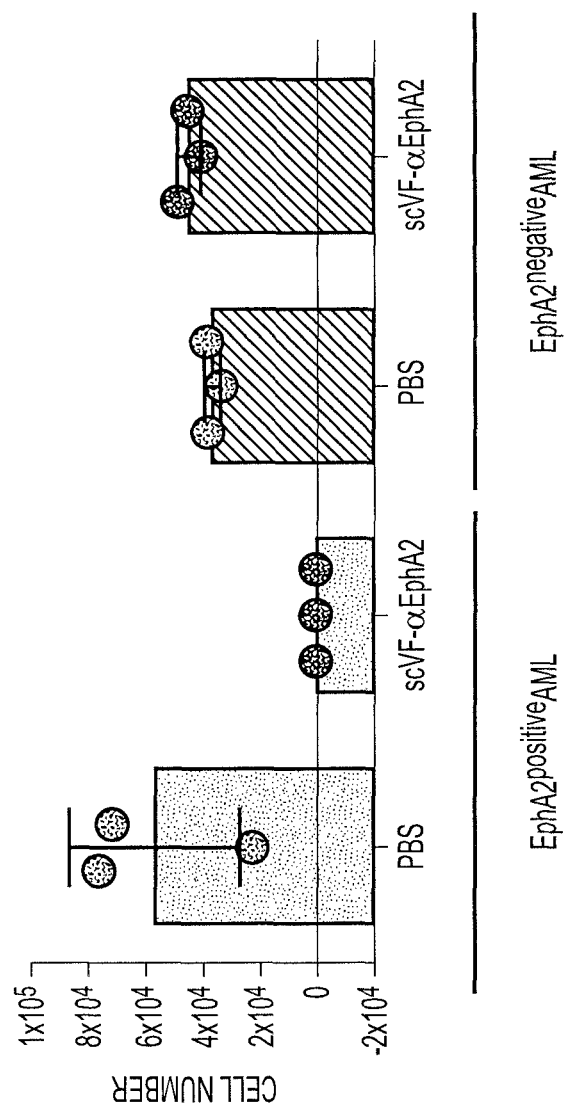
FIG. 7 is a diagram showing that leukemia cells that express high levels of EphA2 do not survive treatment with a single chain anti-EphA2 antibody. The number of viable cells falls from ~60,000 to less than ~1000 cells in 72 hours in comparison to cells that were treated with a buffer control. Cells that express no EphA2 are as viable after treatment with a single chain anti-EphA2 antibody or the buffer.

After validating that EphA2 is expressed in leukemia cells, a set of single-chain antibodies (scFv) specific to EphA2 was tested that have shown activity against Raji cells (discussed above). Two single-chain variable fragments (G2 and D2) were tested on samples with low and high expression of EphA2. The samples were incubated in triplicate in the serum free IMDM medium supplemented with cytokines. The single chain fragments were tested at 0.5 µg and 1.0 µg and evaluated at 24 and 72 hours after culture. Exposure to D2 resulted in a significant decrease in cell number after 72 hours in culture, 52.6% and 99.3% relative to vehicle control treatment for 0.5 ug and 1.0 ug respectively in EphA2-high AML cells (see FIG. 7). That suggests that the single-chain antibodies (scFv) specific to EphA2 tested are lethal to AML cells that express high levels of EphA2. This shows that AML cells that express EphA2 can be targeted using single-chain antibodies (scFv) specific to EphA2 that have shown activity against Raji cells.

Example 9

Generation of Bispecific Anti-EphA2-Anti-CD20 Antibody

The specific anti-EphA2 single-chain antibody can be used in an innovative and tumor-selective treatment by exploring the therapeutic activity of an anti-EphA2/anti-CD20 fusion antibody construct. To target the anti-EphA2 antibody selectively to the CD20 positive lymphoma cells, it was fused to an anti-CD20 scFv antibody (having the amino acid sequences of "qivlsqspailsaspgekvtmtcrasssvsyihwfqqkpgsspkpwiyatsnlasgvpvrfsgsgsgtsysltisrveaedaatyy cqqwtsnpptfgggtkleikrtgggsgaggsggggtggggsqvqlqqpgaelvkpgasvkmsckasgytftsynmhwvkqt pgrglewigaiypgngdtsynqkfkgkatltadkssstaymqlssltsedsavyycarstyyggdwyfnvwgagttvtvsa" (SEQ ID NO: 3)). The fusion antibody has the single chain anti-EphA2 antibody fused to the anti-CD20 antibody (rituximab) through a flexible linker, thus offering specific binding properties for both EphA2 and CD-20 (Table 3). The nucleotide sequence encoding the anti-EphA2/anti-CD20 fusion protein is shown in SEQ ID NO:2, which includes the SfiI sites for cloning. The complete amino acid sequence encoded by SEQ ID NO:2 is shown in SEQ ID NO:4. The nucleotide sequence encoding the antibody portion of the fusion protein is shown in SEQ ID NO:8. The complete amino acid sequence encoded by SEQ ID NO:8 is shown in SEQ ID NO:9. The anti-CD20/anti-EphA2 fusion construct defines a novel lymphoma therapeutic reagent by combining the targeted delivery and the destructive B-cell effects of a well-known and of a newly identified antibody and, therefore, offers significant advance over other approaches and an immense therapeutic potential.

TABLE 3

Sequence of the scFv_rituximab-scFv_D2-construct for bacterial expression. Schematically, the composition of the construct is: SfiI site-scFv_rituximab-6aa linker-scFv_D2-SfiI. The SfiI-sites underlined in the nucleotide sequence below. The first SfiI site is located within the bacterial signal sequence pelB. The last amino acids of the pelB-signal sequence are encoded by this construct (the amino acids marked are underlined in the amino acid sequence below), the rest come from the expression vector. The linker amino acids are in bold enlarged. Amino acid sequence before the linker is anti-CD20 amino acid sequence. Amino acid sequence after the linker is anti-EphA2 amino acid sequence. The underlined sequence in SEQ ID NO: 4 is the signal peptide. Amino acids introduced by the SfiI-cloning site and forming a linker to 6xHis tag (the tag encoding sequence in the vector) are shown at the end in bold italics.

Nucleotide Sequence (SEQ ID NO: 2):
aaaagc<u>ggcccagccggcc</u>atggcgcaaattgttctctcccagtctcag
caatcctgtctgcatctccaggggagaaggtcacaatgacttgcagggcc
agctcaagtgtaagttacatacactggttccagcagaagccaggatcctc
ccccaaaccctggatttatgccacatccaacctggcttctggagtccctg
tacgcttcagtggcagtgggtctgggacctcttactctctcacaatcagc
agagtggaggctgaagatgctgccacttattactgccagcagtggacaag
taacccaccgacgttcggtggaggcaccaagctggaaatcaaacgcacag
gtggtggcggcagtggcgccggtgggtctggaggtggcggtaccggtggc
ggagggtcacaggtgcagctgcagcagcccggcgctgaactagtaaaacc
gggcgcttcagtgaaaatgtcctgcaaagcatccggctacaccttcacct
catacaatatgcactgggtaaaacagacaccgggccgaggcctggaatgg
atcggcgaatctacccgggcaacggcgacacctcatacaaccaaaaatt
caaaggcaaagcaaccctcaccgcagacaaatcctcatccacagcttaca
tgcaactgtcctccctgacatccgaagactcagcagtgtactactgcgct
cgctccacatactatggaggcgactggtacttcaacgtgtggggcgcagg
caccacagtgaccgtgtccgctggtggtggcggcagtggcgaatcgtgc
tgacccaatctccgggcacactgagcttgtctccgggcgaacgtgcgacc
cttagctgcagagccagccagtcggtgtccagctcgaaccttgcgtggta
tcaacagaaaccaggtcaagcacctcgcctgctgatttatggcgcctctt
cacgtgccactggggtcccggatcgctttagcggctctggcagtggcacc
gatttactctgaccatttcccgtctggaaccggaagacttcgcggtgta
ctattgtcagcagtcctccagctatccttggacctttggccaggggacga
aagtcgagattaaacgcacaggtggtggcggcagtggcgccggtgggtct
ggaggtggcggtaccggtggcggagggtcagaggtacagctgcttgaaag
cggcggtggcctggtgcaacccgggtgggagcctgcgtctgtcgtgcgcag
cctccggatttacgttctcccgttactggatgcactgggtccgtcaggct
ccaggtaagggtctcgagtgggtcagttctatctctccgtacgacgggga
aacgaactatgcagatagcgtgaaggggtcgcttcaccatctccgggaca
attcgaagaacacactgtatctccaaatgaactcgcttcgtgctgaggac
actgccgtctactactgtgctcgtatctctgaatggtacaactgggctgt
tgacgttttcgactactggggtcagggtacactagtcaccgtgagct<u>cgg
cctcggggg</u>ccaaaa Amino acid sequence (SEQ ID NO: 4):
<u>kaaqpamaq</u>ivlsqspailsaspgekvtmtcrassssysyihwfqqkpgss
pkpwiyatsnlasgvpvrfsgsgsgtsysltisrveaedaatyycqqwts
npptfgggtkleikrtggggsgaggsggggtggggsqvqlqqpgaelvkp
gasvkmsckasgytftsynmhwvkqtpgrglewigaiypgngdtsynqkf
kgkatltadkssstaymqlssltsedsavyycarstyyggdwyfnvwgag
ttvtvsagggggseivltqspgtlslspgeratlscrasqsysssnlawy
qqkpgqaprlliygassratgvpdrfsgsgsgtdftltisrlepedfavy
ycqqsssypwtfgqgtkveikrtgggsgaggsggggtggggsevqlles
ggglvqpggslrlscaasgfifsrywmhwvrqapgkglewvssispydge
tnyadsvkgrftisrdnskntlylqmnslraedtavyycarisewynwav
dvfdywgqgtivtvssasgak

The following sequences represent additional EphA2-specific scFv sequences that can be used in aspects of the application, including the creation of fusion proteins:

SEQ ID NO: 5
EIVLTQSPGTLSLSPGERATLSCRASQSVSSSYLHWYQQKPGQAPRLL

IYGASSRATGVPDRFSGSGSGTDFTLTISRLEPEDFAVYYCQQHYSIP

STFGQGTKVEIKRTGGGGSGAGGSGGGGTGGGGSEVQLLESGGGLVQP

GGSLRLSCAASGFTFSSYLMHWVRQAPGKGLEWVSLITPSGGSTHYAD

SVKGRFTISRDNSKNTLYLQMNSLRAEDTAVYYCARSGFGYWGQGTLV

TVSSAS

SEQ ID NO: 6
EIVLTQSPGTLSLSPGERATLSCRASQSVSSSTLNWYQQKPGQAPRLL

IYGASSRATGVPDRFSGSGSGTDFTLTISRLEPEDFAVYYCHQDNSNP

RTFGQGTKVEIKRTGGGGSGAGGSGGGGTGGGGSEVQLLESGGGLVQP

GGSLRLSCAASGFTFSSYLMNWVRQAPGKGLEWVSEINPSGGSTYYAD

SVKGRFTISRDNSKNTLYLQMNSLRAEDTAVYYCASWGPWFDYWGQGT

LVTVSSAS

SEQ ID NO: 7
EIVLTQSPGTLSLSPGERATLSCRASQSVSSSSLNWYQQKPGQAPRLL

IYGASSRATGVPDRFSGSGSGTDFTLTISRLEPEDFAVYYCLQRYYSP

RTFGQGTKVEIKRTGGGGSGAGGSGGGGTGGGGSEVQLLESGGGLVQP

GGSLRLSCAASGFTFSSYLMSWVRQAPGKGLEWVSSIDSSGGSTYYAD

SVKGRFTISRDNSKNTLYLQMNSLRAEDTAVYYCGRSTPLGDYWGQGT

LVTVSSAS

Each of SEQ ID NO:1, SEQ ID NO:3, SEQ ID NO:5, SEQ ID NO:6, and SEQ ID NO:7 can be used for any of the aspects or embodiments of the application. In further embodiments, the anti-single-chain EphA2 antibody has an amino acid sequence with at least about 70%, 80%, 90%, 95%, 98%, 99% identical to SEQ ID NO:1, SEQ ID NO:3, SEQ ID NO:5, SEQ ID NO:6, or SEQ ID NO:7.

Example 10

Testing of Bispecific Anti-EphA2-Anti-CD20 Antibody in Cells Lines

Lymphoma cell lines Raji, DHL-10, DoHH2, Karpas 422, Ly-19, or Toledo (at $5 \times 10^4$ per ml) and patient AML leukemia cells are treated with various concentrations (1, 5, and 10 µg/ml) of the purified anti-CD20/EphA2 bispecific antibody preparations and analyzed after 24 h, 48 h and 72 h using cell viability, apoptosis, and cell proliferation assays with standard methods, such as Guava ViaCount (cat. 4000-0041).

Example 11

Testing of Bispecific Anti-EphA2-Anti-CD20 Antibody in Mice

Bispecific antibody is tested in a vavPBcl2 mouse model. Xenografts are done by injecting (s.c.) Raji or SU-DHL-10 human lymphoma cells mixed with matrigel into the flanks of NOD/SCID mice. When the tumor size is more than 1 cm³, mice are treated on alternate days with three intratumoral injections of various concentrations (up to 20 µg for three days) of the antibody. Tumors are analyzed for weight and volumes, apoptosis, architecture, and ERK phosphorylation.

Systemic and dosed (1 µg and up, i.v. for 5 days) application of the bispecific antibody into the xenografted mice by tail vein injection is performed. Tumors are analyzed for weight and volumes, apoptosis, architecture, and ERK phosphorylation.

Toxicity of the antibody is tested by treating the animals with twice the therapeutic dose and analyzing necropsy (micro- or macroscopic organ damage) and serum chemistry (e.g. glucose level and mean corpuscular hemoglobin) at 24 h or 7 days after treatment.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A protein comprising an anti-EphA2 scFv domain comprising the amino acid sequence of SEQ ID NO: 1, 5, 6 or 7.

2. A protein according to claim 1, further comprising an anti-CD20 scFV domain and a peptide linker, wherein the peptide linker connects the anti-EphA2 scFv domain to the anti-CD20 scFV domain.

3. A protein according to claim 2, wherein the anti-EphA2 scFv domain comprises the amino acid sequence of SEQ ID NO: 1.

4. A protein according to claim 2, further comprising an N-terminal signal peptide sequence for secretion of the protein.

5. A polynucleotide comprising a nucleotide sequence encoding the protein of claim 2.

6. An expression vector comprising the polynucleotide of claim 5 operably linked to one or more regulatory sequences sufficient for expressing the protein in a cell.

7. A cultured cell comprising the expression vector of claim 6.

8. A method for producing a protein comprising an anti-EphA2 scFv domain, said method comprising culturing the cell of claim 7 to produce the protein.

9. A method of inhibiting the proliferation of lymphoma or leukemia cells that express EphA2, the method comprising contacting the lymphoma or leukemia cells in vitro with an effective amount of a protein according to claim 2.

10. A protein according to claim 1, further comprising an anti-CD20 scFV domain comprising the amino acid sequence of SEQ ID NO:3 and a peptide linker, wherein the peptide linker connects the anti-EphA2 scFv domain to the anti-CD20 scFV domain.

11. A protein according to claim 10, wherein the anti-EphA2 scFv domain comprises the amino acid sequence of SEQ ID NO: 1.

12. A protein according to claim 10, comprising the amino acid sequence of SEQ ID NO:4 or SEQ ID NO:9.

13. A protein according to claim 10, further comprising an N-terminal signal peptide sequence for secretion of the protein.

14. A polynucleotide comprising a nucleotide sequence encoding the protein of claim 10.

15. An expression vector comprising the polynucleotide of claim 14 operably linked to one or more regulatory sequences sufficient for expressing the protein in a cell.

16. A cultured cell comprising the expression vector of claim 13.

17. A method for producing a protein comprising an anti-EphA2 scFv domain, said method comprising culturing the cell of claim 16 to produce the protein.

18. A polynucleotide according to claim 14, wherein the polynucleotide comprises SEQ ID NO:2 or SEQ ID NO:8.

19. An expression vector comprising the polynucleotide of claim 18 operably linked to one or more regulatory sequences sufficient for expressing the protein in a cell.

20. A cultured cell comprising the expression vector of claim 19.

21. A method for producing a protein comprising an anti-EphA2 scFv domain, said method comprising culturing the cell of claim 20 to produce the protein.

22. A method of inhibiting the proliferation of lymphoma or leukemia cells that express EphA2, the method comprising contacting the lymphoma or leukemia cells in vitro with an effective amount of a protein according to claim 10.

23. A protein according to claim 1, wherein the anti-EphA2 scFv domain comprises the amino acid sequence of SEQ ID NO: 1.

24. A protein according to claim 1, further comprising an N-terminal signal peptide sequence for secretion of the protein.

25. A polynucleotide comprising a nucleotide sequence encoding the protein of claim 1.

26. An expression vector comprising the polynucleotide of claim 25 operably linked to one or more regulatory sequences sufficient for expressing the protein in a cell.

27. A method of inhibiting the proliferation of lymphoma or leukemia cells that express EphA2, the method comprising contacting the lymphoma or leukemia cells in vitro with an effective amount of a protein according to claim 1.

* * * * *

SEQUENCE LISTING

```
<160> NUMBER OF SEQ ID NOS: 9

<210> SEQ ID NO 1
<211> LENGTH: 253
<212> TYPE: PRT
<213> ORGANISM: Artificial Sequence
<220> FEATURE:
<223> OTHER INFORMATION: Synthetic

<400> SEQUENCE: 1

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Ser Tyr Pro
                85                  90                  95

Trp Thr Phe Gly Gln Gly Thr Lys Val Glu Ile Lys Arg Thr Gly Gly
            100                 105                 110

Gly Gly Ser Gly Ala Gly Gly Ser Gly Gly Gly Thr Gly Gly Gly
        115                 120                 125

Gly Ser Glu Val Gln Leu Leu Glu Ser Gly Gly Gly Leu Val Gln Pro
    130                 135                 140

Gly Gly Ser Leu Arg Leu Ser Cys Ala Ala Ser Gly Phe Thr Phe Ser
145                 150                 155                 160

Arg Tyr Trp Met His Trp Val Arg Gln Ala Pro Gly Lys Gly Leu Glu
                165                 170                 175

Trp Val Ser Ser Ile Ser Pro Tyr Asp Gly Glu Thr Asn Tyr Ala Asp
            180                 185                 190

Ser Val Lys Gly Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220

Tyr Cys Ala Arg Ile Ser Glu Trp Tyr Asn Trp Ala Val Asp Val Phe
225                 230                 235                 240

Asp Tyr Trp Gly Gln Gly Thr Leu Val Thr Val Ser Ser
                245                 250

<210> SEQ ID NO 2
<211> LENGTH: 1565
<212> TYPE: DNA
<213> ORGANISM: Artificial Sequence
<220> FEATURE:
```

<223> OTHER INFORMATION: Synthetic

<400> SEQUENCE: 2

| | | | | | |
|---|---|---|---|---|---|
| aaaagcggcc | cagccggcca | tggcgcaaat | tgttctctcc | cagtctccag | caatcctgtc | 60 |
| tgcatctcca | ggggagaagg | tcacaatgac | ttgcagggcc | agctcaagtg | taagttacat | 120 |
| acactggttc | cagcagaagc | caggatcctc | ccccaaaccc | tggatttatg | ccacatccaa | 180 |
| cctggcttct | ggagtccctg | tacgcttcag | tggcagtggg | tctgggacct | cttactctct | 240 |
| cacaatcagc | agagtggagg | ctgaagatgc | tgccacttat | tactgccagc | agtggacaag | 300 |
| taacccaccg | acgttcggtg | gaggcaccaa | gctggaaatc | aaacgcacag | gtggtggcgg | 360 |
| cagtggcgcc | ggtgggtctg | gaggtggcgg | taccggtggc | ggagggtcac | aggtgcagct | 420 |
| gcagcagccc | ggcgctgaac | tagtaaaacc | gggcgcttca | gtgaaaatgt | cctgcaaagc | 480 |
| atccggctac | accttcacct | catacaatat | gcactgggta | aaacagacac | cgggccgagg | 540 |
| cctggaatgg | atcggcgcaa | tctacccggg | caacggcgac | acctcataca | accaaaaatt | 600 |
| caaaggcaaa | gcaaccctca | ccgcagacaa | atcctcatcc | acagcttaca | tgcaactgtc | 660 |
| ctccctgaca | tccgaagact | cagcagtgta | ctactgcgct | cgctccacat | actatggagg | 720 |
| cgactggtac | ttcaacgtgt | ggggcgcagg | caccacagtg | accgtgtccg | ctggtggtgg | 780 |
| cggcagtggc | gagatcgtgc | tgacccaatc | tccgggcaca | ctgagcttgt | ctccgggcga | 840 |
| acgtgcgacc | cttagctgca | gagccagcca | gtcggtgtcc | agctcgaacc | ttgcgtggta | 900 |
| tcaacagaaa | ccaggtcaag | cacctcgcct | gctgatttat | ggcgcctctt | cacgtgccac | 960 |
| tggggtcccg | gatcgcttta | gcggctctgg | cagtggcacc | gatttactc | tgaccatttc | 1020 |
| ccgtctggaa | ccggaagact | tcgcggtgta | ctattgtcag | cagtcctcca | gctatccttg | 1080 |
| gacctttggc | caggggacga | agtcgagat | taaacgcaca | ggtggtggcg | gcagtggcgc | 1140 |
| cggtgggtct | ggaggtggcg | gtaccggtgg | cggagggtca | gaggtacagc | tgcttgaaag | 1200 |
| cggcggtggc | ctggtgcaac | cgggtgggag | cctgcgtctg | tcgtgcgcag | cctccggatt | 1260 |
| tacgttctcc | cgttactgga | tgcactgggt | ccgtcaggct | ccaggtaagg | gtctcgagtg | 1320 |
| ggtcagttct | atctctccgt | acgacgggga | aacgaactat | gcagatagcg | tgaagggtcg | 1380 |
| cttcaccatc | tcccgggaca | attcgaagaa | cacactgtat | ctccaaatga | actcgcttcg | 1440 |
| tgctgaggac | actgccgtct | actactgtgc | tcgtatctct | gaatggtaca | actgggctgt | 1500 |
| tgacgttttc | gactactggg | gtcagggtac | actagtcacc | gtgagctcgg | cctcgggggc | 1560 |
| caaaa | | | | | | 1565 |

<210> SEQ ID NO 3
<211> LENGTH: 249
<212> TYPE: PRT
<213> ORGANISM: Artificial Sequence
<220> FEATURE:
<223> OTHER INFORMATION: Synthetic

<400> SEQUENCE: 3

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

```
Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys Arg Thr Gly Gly Gly Gly
            100                 105                 110

Ser Gly Ala Gly Gly Ser Gly Gly Gly Thr Gly Gly Gly Gly Gly Ser
            115                 120                 125

Gln Val Gln Leu Gln Gln Pro Gly Ala Glu Leu Val Lys Pro Gly Ala
130                 135                 140

Ser Val Lys Met Ser Cys Lys Ala Ser Gly Tyr Thr Phe Thr Ser Tyr
145                 150                 155                 160

Asn Met His Trp Val Lys Gln Thr Pro Gly Arg Gly Leu Glu Trp Ile
                165                 170                 175

Gly Ala Ile Tyr Pro Gly Asn Gly Asp Thr Ser Tyr Asn Gln Lys Phe
            180                 185                 190

Lys Gly Lys Ala Thr Leu Thr Ala Asp Lys Ser Ser Ser Thr Ala Tyr
            195                 200                 205

Met Gln Leu Ser Ser Leu Thr Ser Glu Asp Ser Ala Val Tyr Tyr Cys
        210                 215                 220

Ala Arg Ser Thr Tyr Tyr Gly Gly Asp Trp Tyr Phe Asn Val Trp Gly
225                 230                 235                 240

Ala Gly Thr Thr Val Thr Val Ser Ala
                245

<210> SEQ ID NO 4
<211> LENGTH: 521
<212> TYPE: PRT
<213> ORGANISM: Artificial Sequence
<220> FEATURE:
<223> OTHER INFORMATION: Synthetic

<400> SEQUENCE: 4

Lys Ala Ala Gln Pro Ala Met Ala Gln Ile Val Leu Ser Gln Ser Pro
 1               5                  10                  15

Ala Ile Leu Ser Ala Ser Pro Gly Glu Lys Val Thr Met Thr Cys Arg
                20                  25                  30

Ala Ser Ser Ser Val Ser Tyr Ile His Trp Phe Gln Gln Lys Pro Gly
            35                  40                  45

Ser Ser Pro Lys Pro Trp Ile Tyr Ala Thr Ser Asn Leu Ala Ser Gly
        50                  55                  60

Val Pro Val Arg Phe Ser Gly Ser Gly Ser Gly Thr Ser Tyr Ser Leu
 65                  70                  75                  80

Thr Ile Ser Arg Val Glu Ala Glu Asp Ala Ala Thr Tyr Tyr Cys Gln
                 85                  90                  95

Gln Trp Thr Ser Asn Pro Pro Thr Phe Gly Gly Gly Thr Lys Leu Glu
            100                 105                 110

Ile Lys Arg Thr Gly Gly Gly Gly Ser Gly Ala Gly Gly Ser Gly Gly
        115                 120                 125

Gly Gly Thr Gly Gly Gly Gly Ser Gln Val Gln Leu Gln Gln Pro Gly
130                 135                 140

Ala Glu Leu Val Lys Pro Gly Ala Ser Val Lys Met Ser Cys Lys Ala
145                 150                 155                 160

Ser Gly Tyr Thr Phe Thr Ser Tyr Asn Met His Trp Val Lys Gln Thr
                165                 170                 175
```

```
Pro Gly Arg Gly Leu Glu Trp Ile Gly Ala Ile Tyr Pro Gly Asn Gly
            180                 185                 190

Asp Thr Ser Tyr Asn Gln Lys Phe Lys Gly Lys Ala Thr Leu Thr Ala
        195                 200                 205

Asp Lys Ser Ser Ser Thr Ala Tyr Met Gln Leu Ser Ser Leu Thr Ser
210                 215                 220

Glu Asp Ser Ala Val Tyr Tyr Cys Ala Arg Ser Thr Tyr Tyr Gly Gly
225                 230                 235                 240

Asp Trp Tyr Phe Asn Val Trp Gly Ala Gly Thr Val Thr Val Ser
                245                 250                 255

Ala Gly Gly Gly Ser Gly Glu Ile Val Leu Thr Gln Ser Pro Gly
            260                 265                 270

Thr Leu Ser Leu Ser Pro Gly Glu Arg Ala Thr Leu Ser Cys Arg Ala
        275                 280                 285

Ser Gln Ser Val Ser Ser Asn Leu Ala Trp Tyr Gln Gln Lys Pro
290                 295                 300

Gly Gln Ala Pro Arg Leu Leu Ile Tyr Gly Ala Ser Ser Arg Ala Thr
305                 310                 315                 320

Gly Val Pro Asp Arg Phe Ser Gly Ser Gly Ser Gly Thr Asp Phe Thr
                325                 330                 335

Leu Thr Ile Ser Arg Leu Glu Pro Glu Asp Phe Ala Val Tyr Tyr Cys
            340                 345                 350

Gln Gln Ser Ser Ser Tyr Pro Trp Thr Phe Gly Gln Gly Thr Lys Val
        355                 360                 365

Glu Ile Lys Arg Thr Gly Gly Gly Gly Ser Gly Ala Gly Gly Ser Gly
            370                 375                 380

Gly Gly Gly Thr Gly Gly Gly Ser Glu Val Gln Leu Leu Glu Ser
385                 390                 395                 400

Gly Gly Gly Leu Val Gln Pro Gly Gly Ser Leu Arg Leu Ser Cys Ala
                405                 410                 415

Ala Ser Gly Phe Thr Phe Ser Arg Tyr Trp Met His Trp Val Arg Gln
            420                 425                 430

Ala Pro Gly Lys Gly Leu Glu Trp Val Ser Ser Ile Ser Pro Tyr Asp
        435                 440                 445

Gly Glu Thr Asn Tyr Ala Asp Ser Val Lys Gly Arg Phe Thr Ile Ser
450                 455                 460

Arg Asp Asn Ser Lys Asn Thr Leu Tyr Leu Gln Met Asn Ser Leu Arg
465                 470                 475                 480

Ala Glu Asp Thr Ala Val Tyr Tyr Cys Ala Arg Ile Ser Glu Trp Tyr
                485                 490                 495

Asn Trp Ala Val Asp Val Phe Asp Tyr Trp Gly Gln Gly Thr Leu Val
            500                 505                 510

Thr Val Ser Ser Ala Ser Gly Ala Lys
        515                 520

<210> SEQ ID NO 5
<211> LENGTH: 246
<212> TYPE: PRT
<213> ORGANISM: Artificial Sequence
<220> FEATURE:
<223> OTHER INFORMATION: Synthetic

<400> SEQUENCE: 5

Glu Ile Val Leu Thr Gln Ser Pro Gly Thr Leu Ser Leu Ser Pro Gly
1               5                   10                  15
```

Glu Arg Ala Thr Leu Ser Cys Arg Ala Ser Gln Ser Val Ser Ser Ser
            20                  25                  30

Tyr Leu His Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Tyr Ser Ile Pro
                85                  90                  95

Ser Thr Phe Gly Gln Gly Thr Lys Val Glu Ile Lys Arg Thr Gly Gly
            100                 105                 110

Gly Gly Ser Gly Ala Gly Gly Ser Gly Gly Gly Gly Thr Gly Gly Gly
            115                 120                 125

Gly Ser Glu Val Gln Leu Leu Glu Ser Gly Gly Gly Leu Val Gln Pro
        130                 135                 140

Gly Gly Ser Leu Arg Leu Ser Cys Ala Ala Ser Gly Phe Thr Phe Ser
145                 150                 155                 160

Ser Tyr Leu Met His Trp Val Arg Gln Ala Pro Gly Lys Gly Leu Glu
                165                 170                 175

Trp Val Ser Leu Ile Thr Pro Ser Gly Gly Ser Thr His Tyr Ala Asp
            180                 185                 190

Ser Val Lys Gly Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220

Tyr Cys Ala Arg Ser Gly Phe Gly Tyr Trp Gly Gln Gly Thr Leu Val
225                 230                 235                 240

Thr Val Ser Ser Ala Ser
            245

<210> SEQ ID NO 6
<211> LENGTH: 248
<212> TYPE: PRT
<213> ORGANISM: Artificial Sequence
<220> FEATURE:
<223> OTHER INFORMATION: Synthetic

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Thr Leu Asn Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Asp Asn Ser Asn Pro
                85                  90                  95

Arg Thr Phe Gly Gln Gly Thr Lys Val Glu Ile Lys Arg Thr Gly Gly
            100                 105                 110

Gly Gly Ser Gly Ala Gly Gly Ser Gly Gly Gly Gly Thr Gly Gly Gly
            115                 120                 125

```
Gly Ser Glu Val Gln Leu Leu Glu Ser Gly Gly Leu Val Gln Pro
    130                 135                 140
Gly Gly Ser Leu Arg Leu Ser Cys Ala Ala Ser Gly Phe Thr Phe Ser
145                 150                 155                 160
Ser Tyr Leu Met Asn Trp Val Arg Gln Ala Pro Gly Lys Gly Leu Glu
                165                 170                 175
Trp Val Ser Glu Ile Asn Pro Ser Gly Gly Ser Thr Tyr Tyr Ala Asp
            180                 185                 190
Ser Val Lys Gly Arg Phe Thr Ile Ser Arg Asp Asn Ser Lys Asn Thr
        195                 200                 205
Leu Tyr Leu Gln Met Asn Ser Leu Arg Ala Glu Asp Thr Ala Val Tyr
    210                 215                 220
Tyr Cys Ala Ser Trp Gly Pro Trp Phe Asp Tyr Trp Gly Gln Gly Thr
225                 230                 235                 240
Leu Val Thr Val Ser Ser Ala Ser
                245

<210> SEQ ID NO 7
<211> LENGTH: 248
<212> TYPE: PRT
<213> ORGANISM: Artificial Sequence
<220> FEATURE:
<223> OTHER INFORMATION: Synthetic

<400> SEQUENCE: 7

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
                20                  25                  30
Ser Leu Asn Trp Tyr Gln Gln Lys Pro Gly Gln Ala Pro Arg Leu Leu
            35                  40                  45
Ile Tyr Gly Ala Ser Ser Arg Ala Thr Gly Val Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Leu Gln Arg Tyr Tyr Ser Pro
                85                  90                  95
Arg Thr Phe Gly Gln Gly Thr Lys Val Glu Ile Lys Arg Thr Gly Gly
                100                 105                 110
Gly Gly Ser Gly Ala Gly Gly Ser Gly Gly Gly Thr Gly Gly Gly
            115                 120                 125
Gly Ser Glu Val Gln Leu Leu Glu Ser Gly Gly Leu Val Gln Pro
    130                 135                 140
Gly Gly Ser Leu Arg Leu Ser Cys Ala Ala Ser Gly Phe Thr Phe Ser
145                 150                 155                 160
Ser Tyr Leu Met Ser Trp Val Arg Gln Ala Pro Gly Lys Gly Leu Glu
                165                 170                 175
Trp Val Ser Ser Ile Asp Ser Ser Gly Gly Ser Thr Tyr Tyr Ala Asp
            180                 185                 190
Ser Val Lys Gly Arg Phe Thr Ile Ser Arg Asp Asn Ser Lys Asn Thr
        195                 200                 205
Leu Tyr Leu Gln Met Asn Ser Leu Arg Ala Glu Asp Thr Ala Val Tyr
    210                 215                 220
Tyr Cys Gly Arg Ser Thr Pro Leu Gly Asp Tyr Trp Gly Gln Gly Thr
225                 230                 235                 240
```

Leu Val Thr Val Ser Ser Ala Ser
            245

<210> SEQ ID NO 8
<211> LENGTH: 1524
<212> TYPE: DNA
<213> ORGANISM: Artificial Sequence
<220> FEATURE:
<223> OTHER INFORMATION: Synthetic

<400> SEQUENCE: 8

| | | | | | |
|---|---|---|---|---|---|
| caaattgttc | tctcccagtc | tccagcaatc | ctgtctgcat | ctccagggga | gaaggtcaca | 60 |
| atgacttgca | gggccagctc | aagtgtaagt | tacatacact | ggttccagca | gaagccagga | 120 |
| tcctccccca | aaccctggat | ttatgccaca | tccaacctgg | cttctggagt | ccctgtacgc | 180 |
| ttcagtggca | gtgggtctgg | gacctcttac | tctctcacaa | tcagcagagt | ggaggctgaa | 240 |
| gatgctgcca | cttattactg | ccagcagtgg | acaagtaacc | caccgacgtt | cggtggaggc | 300 |
| accaagctgg | aaatcaaacg | cacaggtggt | ggcggcagtg | gcgccggtgg | gtctggaggt | 360 |
| ggcggtaccg | gtggcggagg | gtcacaggtg | cagctgcagc | agcccggcgc | tgaactagta | 420 |
| aaaccgggcg | cttcagtgaa | aatgtcctgc | aaagcatccg | gctacacctt | cacctcatac | 480 |
| aatatgcact | gggtaaaaca | gacaccgggc | cgaggcctgg | aatggatcgg | cgcaatctac | 540 |
| ccgggcaacg | gcgacacctc | atacaaccaa | aaattcaaag | gcaaagcaac | cctcaccgca | 600 |
| gacaaatcct | catccacagc | ttacatgcaa | ctgtcctccc | tgacatccga | agactcagca | 660 |
| gtgtactact | gcgctcgctc | cacatactat | ggaggcgact | ggtacttcaa | cgtgtgggc | 720 |
| gcaggcacca | cagtgaccgt | gtccgctggt | ggtggcggca | gtggcgagat | cgtgctgacc | 780 |
| caatctccgg | gcacactgag | cttgtctccg | ggcgaacgtg | cgacccttag | ctgcagagcc | 840 |
| agccagtcgg | tgtccagctc | gaaccttgcg | tggtatcaac | agaaaccagg | tcaagcacct | 900 |
| cgcctgctga | tttatggcgc | ctcttcacgt | gccactgggg | tcccggatcg | ctttagcggc | 960 |
| tctggcagtg | gcaccgattt | tactctgacc | atttcccgtc | tggaaccgga | agacttcgcg | 1020 |
| gtgtactatt | gtcagcagtc | ctccagctat | ccttggacct | ttggccaggg | gacgaaagtc | 1080 |
| gagattaaac | gcacaggtgg | tggcggcagt | ggcgccggtg | ggtctggagg | tggcggtacc | 1140 |
| ggtggcggag | ggtcagaggt | acagctgctt | gaaagcggcg | gtggcctggt | gcaaccgggt | 1200 |
| gggagcctgc | gtctgtcgtg | cgcagcctcc | ggatttacgt | tctcccgtta | ctggatgcac | 1260 |
| tgggtccgtc | aggctccagg | taagggtctc | gagtgggtca | gttctatctc | tccgtacgac | 1320 |
| ggggaaacga | actatgcaga | tagcgtgaag | ggtcgcttca | ccatctcccg | ggacaattcg | 1380 |
| aagaacacac | tgtatctcca | aatgaactcg | cttcgtgctg | aggacactgc | cgtctactac | 1440 |
| tgtgctcgta | tctctgaatg | gtacaactgg | gctgttgacg | ttttcgacta | ctggggtcag | 1500 |
| ggtacactag | tcaccgtgag | ctcg | | | | 1524 |

<210> SEQ ID NO 9
<211> LENGTH: 508
<212> TYPE: PRT
<213> ORGANISM: Artificial Sequence
<220> FEATURE:
<223> OTHER INFORMATION: Synthetic

<400> SEQUENCE: 9

Gln Ile Val Leu Ser Gln Ser Pro Ala Ile Leu Ser Ala Ser Pro Gly
1               5                   10                  15

-continued

```
Glu Lys Val Thr Met Thr Cys Arg Ala Ser Ser Val Ser Tyr Ile
             20                  25                  30

His Trp Phe Gln Gln Lys Pro Gly Ser Ser Pro Lys Pro Trp Ile Tyr
         35                  40                  45

Ala Thr Ser Asn Leu Ala Ser Gly Val Pro Val Arg Phe Ser Gly Ser
         50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys Arg Thr Gly Gly Gly Gly
             100                 105                 110

Ser Gly Ala Gly Gly Ser Gly Gly Gly Thr Gly Gly Gly Ser
             115                 120                 125

Gln Val Gln Leu Gln Gln Pro Gly Ala Glu Leu Val Lys Pro Gly Ala
         130                 135                 140

Ser Val Lys Met Ser Cys Lys Ala Ser Gly Tyr Thr Phe Thr Ser Tyr
145                 150                 155                 160

Asn Met His Trp Val Lys Gln Thr Pro Gly Arg Gly Leu Glu Trp Ile
                 165                 170                 175

Gly Ala Ile Tyr Pro Gly Asn Gly Asp Thr Ser Tyr Asn Gln Lys Phe
             180                 185                 190

Lys Gly Lys Ala Thr Leu Thr Ala Asp Lys Ser Ser Ser Thr Ala Tyr
             195                 200                 205

Met Gln Leu Ser Ser Leu Thr Ser Glu Asp Ser Ala Val Tyr Tyr Cys
210                 215                 220

Ala Arg Ser Thr Tyr Tyr Gly Gly Asp Trp Tyr Phe Asn Val Trp Gly
225                 230                 235                 240

Ala Gly Thr Thr Val Thr Val Ser Ala Gly Gly Gly Ser Gly Glu
                 245                 250                 255

Ile Val Leu Thr Gln Ser Pro Gly Thr Leu Ser Leu Ser Pro Gly Glu
                 260                 265                 270

Arg Ala Thr Leu Ser Cys Arg Ala Ser Gln Ser Val Ser Ser Ser Asn
                 275                 280                 285

Leu Ala Trp Tyr Gln Gln Lys Pro Gly Gln Ala Pro Arg Leu Leu Ile
         290                 295                 300

Tyr Gly Ala Ser Ser Arg Ala Thr Gly Val Pro Asp Arg Phe Ser Gly
305                 310                 315                 320

Ser Gly Ser Gly Thr Asp Phe Thr Leu Thr Ile Ser Arg Leu Glu Pro
                 325                 330                 335

Glu Asp Phe Ala Val Tyr Tyr Cys Gln Gln Ser Ser Tyr Pro Trp
                 340                 345                 350

Thr Phe Gly Gln Gly Thr Lys Val Glu Ile Lys Arg Thr Gly Gly Gly
         355                 360                 365

Gly Ser Gly Ala Gly Gly Ser Gly Gly Gly Thr Gly Gly Gly
             370                 375                 380

Ser Glu Val Gln Leu Leu Glu Ser Gly Gly Leu Val Gln Pro Gly
385                 390                 395                 400

Gly Ser Leu Arg Leu Ser Cys Ala Ala Ser Gly Phe Thr Phe Ser Arg
                 405                 410                 415

Tyr Trp Met His Trp Val Arg Gln Ala Pro Gly Lys Gly Leu Glu Trp
                 420                 425                 430

Val Ser Ser Ile Ser Pro Tyr Asp Gly Glu Thr Asn Tyr Ala Asp Ser
```

-continued

```
                435                 440                 445
Val Lys Gly Arg Phe Thr Ile Ser Arg Asp Asn Ser Lys Asn Thr Leu
    450                 455                 460

Tyr Leu Gln Met Asn Ser Leu Arg Ala Glu Asp Thr Ala Val Tyr Tyr
465                 470                 475                 480

Cys Ala Arg Ile Ser Glu Trp Tyr Asn Trp Ala Val Asp Val Phe Asp
                485                 490                 495

Tyr Trp Gly Gln Gly Thr Leu Val Thr Val Ser Ser
                500                 505
```